United States Patent [19]

Evans

[11] Patent Number: 5,354,486

[45] Date of Patent: Oct. 11, 1994

[54] PHENOL GROUP-CONTAINING COMPOUNDS AS ANTI-OXIDANTS IN ORGANIC MATERIALS

[75] Inventor: Samuel Evans, Marly, Switzerland

[73] Assignee: Ciba-Geigy Corporation, Ardsley, N.Y.

[21] Appl. No.: 114,115

[22] Filed: Aug. 30, 1993

Related U.S. Application Data

[63] Continuation of Ser. No. 8,060, Jan. 22, 1993, abandoned, which is a continuation of Ser. No. 827,907, Jan. 30, 1992, abandoned, which is a continuation of Ser. No. 423,167, Oct. 18, 1989, abandoned.

[30] Foreign Application Priority Data

Oct. 25, 1988 [CH] Switzerland ............... 3959/88

[51] Int. Cl.$^5$ ................................. C10M 129/76
[52] U.S. Cl. ................................. 252/57; 252/79
[58] Field of Search ........................... 252/57, 79

[56] References Cited

U.S. PATENT DOCUMENTS

| | | | |
|---|---|---|---|
| Re. 27,004 | 12/1970 | Meier | 560/75 |
| 3,247,240 | 4/1966 | Meier et al. | |
| 3,285,855 | 11/1966 | Dexter et al. | 252/57 |
| 3,457,286 | 7/1969 | Dexter et al. | 252/48.6 |
| 3,494,887 | 2/1970 | Dexter et al. | |
| 3,644,482 | 2/1972 | Dexter et al. | |
| 3,954,839 | 5/1976 | Dexter et al. | 252/48.6 |
| 3,962,123 | 6/1976 | DiBattista et al. | |
| 3,984,460 | 10/1976 | Spivack | |
| 4,529,809 | 7/1985 | Irving et al. | |
| 4,652,385 | 3/1987 | Cohen | 252/48.6 |
| 4,699,939 | 10/1987 | Orban et al. | 252/51.5 R |

FOREIGN PATENT DOCUMENTS 288254 10/1988 European Pat. Off.
2028866 3/1980 United Kingdom.

OTHER PUBLICATIONS

Chem. Abstract 111:8445e (1989).
Chem. Abstract 111:155122a (1989).
C.A. 99:161228q (1983).

Primary Examiner—Jerry D. Johnson
Attorney, Agent, or Firm—Luther A. R. Hall

[57] ABSTRACT

Compositions containing a) an organic material subject to oxidative, thermal or actinic degradation and b) compounds of general formula I

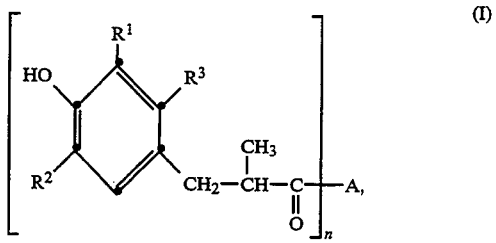

wherein, for example, $R^1$ is alkyl having from 1 to 18 carbon atoms, cycloalkyl having from 5 to 12 carbon atoms, phenyl or aralkyl having from 7 to 9 carbon atoms, $R^2$ is —H, alkyl having from 1 to 18 carbon atoms, cycloalkyl having from 5 to 12 carbon atoms, phenyl or aralkyl having from 7 to 9 carbon atoms, and $R^3$ is —H or $CH_3$, and n is a number from 1 to 4 or 6, when n is 1, A is

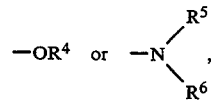

and, for example, $R^4$ is —H, alkyl having from 1 to 45 carbon atoms, cycloalkyl having from 5 to 12 carbon atoms or alkenyl having from 2 to 18 carbon atoms, and each of $R^5$ and $R^6$, independently of the other, is —H, alkyl having from 1 to 20 carbon atoms, phenyl or cycloalkyl having from 5 to 12 carbon atoms, or, when n is 2, for example A is (Abstract continued on next page.)

defined above and $b^1$ is a number from 2 to 10, or, when n is 3, A is
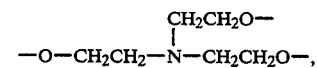
or, when n is 4, A is
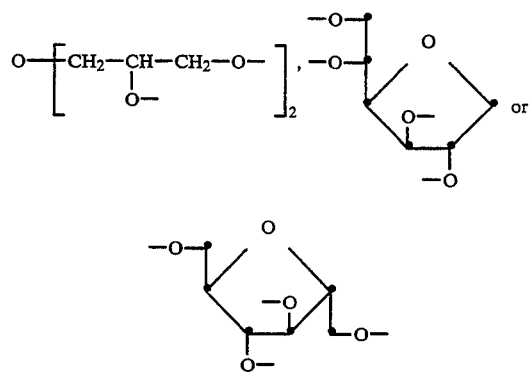
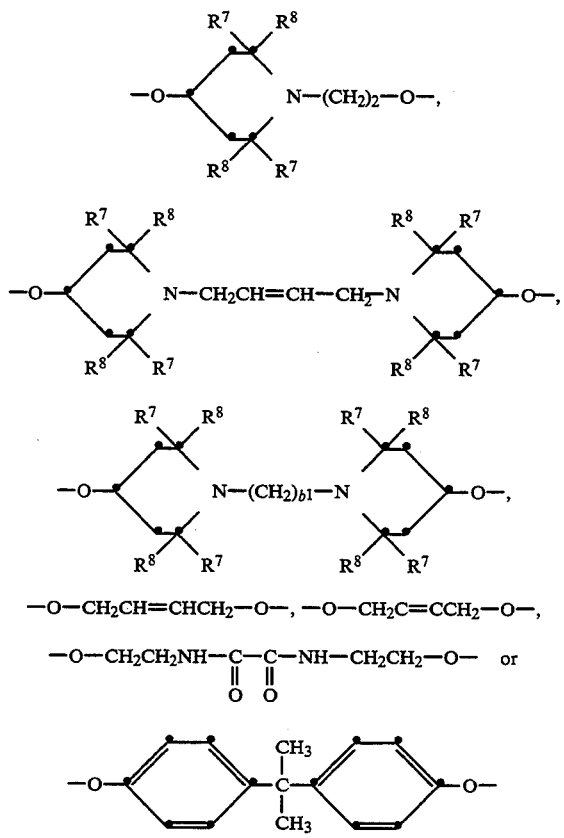
or, when n is 6, A is
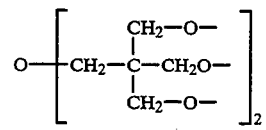
The compounds exhibit anti-oxidative properties in the compositions. Some of the compounds are novel.
6 Claims, No Drawings
wherein a is a number from 1 to 30, x is a number from 2 to 20, B is, for example, —S—, and $R^7$ and $R^8$ are as

PHENOL GROUP-CONTAINING COMPOUNDS AS ANTI-OXIDANTS IN ORGANIC MATERIALS

This is a continuation of application Ser. No. 08/008,060, filed on Jan. 22, 1993, now abandoned, which is a continuation of application Ser. No. 07/827,907, filed on Jan. 30, 1992, now abandoned, which is a continuation of application Ser. No. 07/423,167, filed on Oct. 18, 1989, now abandoned.

The present invention relates to novel compositions containing organic materials subject to oxidative, thermal or actinic degradation and hydroxyphenylcarboxylic acid ester compounds, to novel hydroxyphenylcarboxylic acid compounds and to their use as anti-oxidants.

The stabilisation, for example, of lubricants or plastics with anti-oxidants of the hydroxyphenylcarboxylic acid ester series is known from U.S. Pat. Nos. 3,247,240; 3,644,482; 3,962,123; 3,984,460 and 3,494,887.

DE-A-28 37 141 discloses a lubricating oil formulation consisting of a petroleum distillate, small proportions of other substances and an anti-oxidant, the anti-oxidant containing the α,ω-alkanediol bis-ester of a 2,4,6-trialkylphenolcarboxylic acid.

U.S. Pat. No. 4,529,809 describes a process for the preparation of hydroxyphenylcarboxylic acid esters, wherein methyl, ethyl and propyl esters of 2-methyl-3-(3',5'-di-tert.-butyl-4'-hydroxyphenyl)-propionic acid act as important intermediates in the manufacture of anti-oxidants for polypropylene resins of the pentaerythritol-tetrakis-[2-methyl-3-(3',5'-di-tert.-butyl-4'-hydroxyphenyl)-propionate] type.

Surprisingly, a number of compounds has now been found which exhibit improved properties as anti-oxidants in organic materials, especially in functional fluids and plastics.

The present invention relates to compositions containing a) at least one organic material subject to oxidative, thermal or actinic degradation and b) at least one compound of general formula I

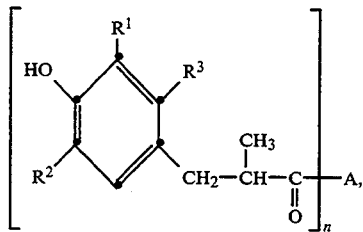

wherein $R^1$ is alkyl having from 1 to 18 carbon atoms, cycloalkyl having from 5 to 12 carbon atoms, phenyl or aralkyl having from 7 to 9 carbon atoms, $R^2$ is —H, alkyl having from 1 to 18 carbon atoms, cycloalkyl having from 5 to 12 carbon atoms, phenyl or aralkyl having from 7 to 9 carbon atoms, and $R^3$ is —H or —CH$_3$, and n is a number from 1 to 4 or 6, and, when n is 1, A is

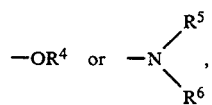

and $R^4$ is —H, alkyl having from 1 to 45 carbon atoms, cycloalkyl having from 5 to 12 carbon atoms, alkenyl having from 2 to 18 carbon atoms,

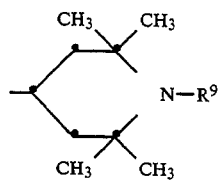

or —CH$_2$CH$_2$—XR$^{5a}$, and each of $R^5$ and $R^6$, independently of the other, is —H, alkyl having from 1 to 20 carbon atoms, phenyl, cycloalkyl having from 5 to 12 carbon atoms, $C_1$–$C_4$alkyl-substituted cycloalkyl having from 5 to 12 carbon atoms, alkenyl having from 3 to 8 carbon atoms, aralkyl having from 7 to 10 carbon atoms or

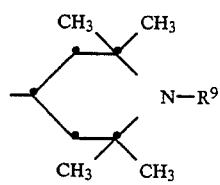

and, in addition, $R^5$ is —NH$_2$, $R^9$ is —H, alkyl having from 1 to 8 carbon atoms,

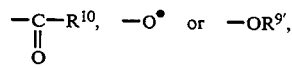

wherein $R^{9'}$ is —H, alkyl having from 1 to 25 carbon atoms or

X is

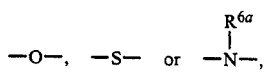

$R^{5a}$ is

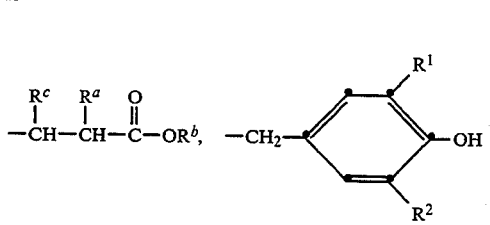

—H, alkyl having from 1 to 24 carbon atoms, phenyl, cycloalkyl having from 5 to 12 carbon atoms or

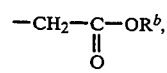

and $R^{10}$ is alkyl having from 1 to 20 carbon atoms, $R^a$ is —H or —CH$_3$, $R^b$ is —H or alkyl having from 1 to 24 carbon atoms and $R^c$ is —H or —CH$_3$, with the proviso that $R^a$ and $R^c$ are not —CH$_3$ at the same time, and $R^{6a}$ is alkyl having from 1 to 18 carbon atoms, phenyl, phenyl substituted by one or more alkyl groups having a total of from 1 to 24 carbon atoms, or $C_5$-$C_8$cycloalkyl, or, when n is 2, A is

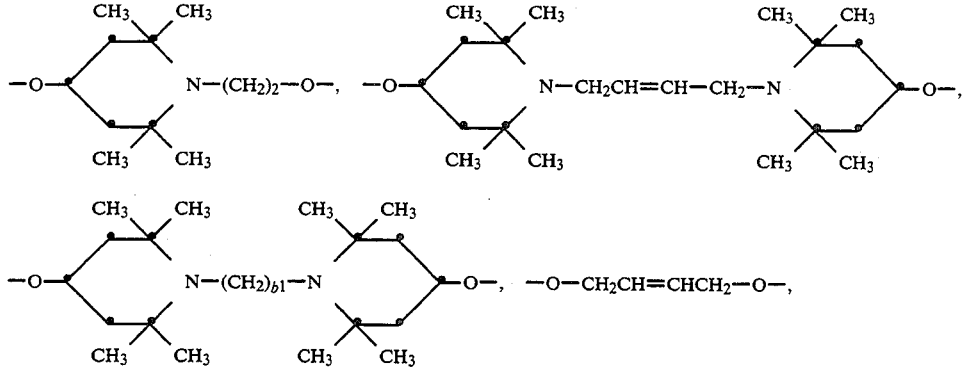

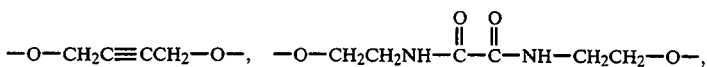

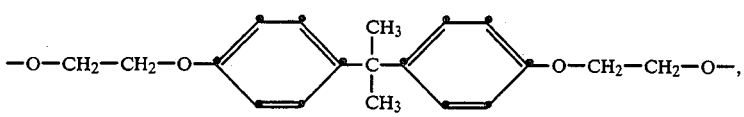

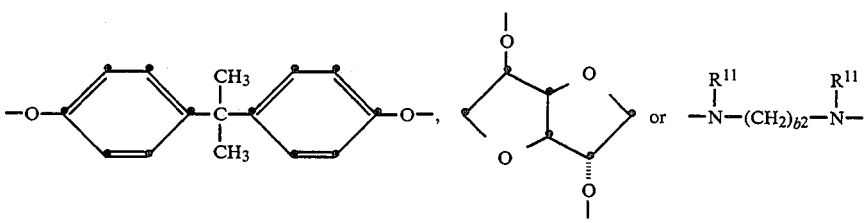

wherein a is a number from 1 to 30, x is a number from 2 to 20, B is

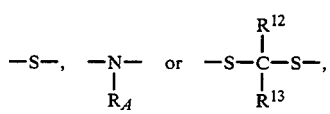

$R_A$ is alkyl having from 1 to 20 carbon atoms, phenyl, phenyl substituted by one or more alkyl groups having a total of from 1 to 20 carbon atoms, cyclohexyl or

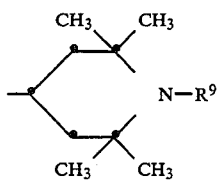

and each of $R^{11}$, $R^{12}$ and $R^{13}$, independently of the others, is —H, alkyl having from 1 to 12 carbon atoms or phenyl, or $R^{12}$ and $R^{13}$ together with the carbon atom to which they are bonded form a cycloalkyl ring having from 5 to 12 carbon atoms, $b^1$ is a number from 2 to 10 and $b^2$ is a number from 0 to 6, or, when n is 3, A is $$-O-CH_2-\underset{\underset{O-}{|}}{CH}-CH_2-O-,$$

or, when n is 4, A is

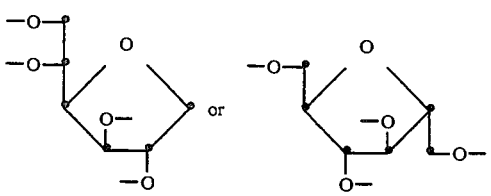

or, when n is 6, A is

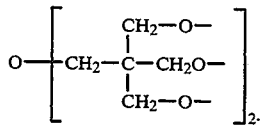

If $R^1$, $R^2$ and $R^{6a}$ are, for example, alkyl having from 1 to 18 carbon atoms, then the alkyl group can be straight-chain or branched and can be, for example: methyl, ethyl, propyl, isopropyl, n-butyl, isobutyl, tert.- butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl. Alkyl having from 1 to 12 carbon atoms is preferred, and alkyl having from 1 to 8 carbon atoms is especially preferred.

For $R^1$ and $R^2$, those alkyl groups from the above list of examples which have from 1 to 8 carbon atoms are to be regarded as advantageous and those having from 1 to 4 carbon atoms are to be regarded as preferred. The tert.-butyl group is especially preferred for $R^1$ and $R^2$.

$R^4$ is, for example, straight-chain or branched alkyl having from 1 to 45 carbon atoms. Examples thereof are those indicated for $R^1$ and $R^2$ and also eicosyl, hemicosyl, docosyl, triacontyl, etc. Preferably, $R^4$ as alkyl is $C_1$–$C_{20}$alkyl, especially $C_1$–$C_{18}$alkyl.

$R_A$, $R^5$, $R^6$ and $R^{10}$ can be alkyl having from 1 to 20 carbon atoms, straight-chain or branched alkyl groups being intended and reference being made to the above list of examples for $R^1$ and $R^2$, supplemented by the further example of eicosyl. Alkyl groups having from 1 to 12 carbon atoms are preferred.

$R^9$ or $R^{9'}$ is, for example, alkyl having from 1 to 8 carbon atoms, the alkyl groups being straight-chain or branched and being methyl, ethyl, propyl, isopropyl, n-butyl, isobutyl, tert.-butyl, pentyl, isopentyl, hexyl, heptyl, octyl, 2-ethylhexyl, 2-ethylbutyl, isoamyl, 1-methyl-pentyl, 1,3-dimethylbutyl, 1,1,3,3-tetramethylbutyl, 1-methylhexyl, isoheptyl or 1-methylheptyl.

An advantageous radical for $R^9$ is alkyl having from 1 to 4 carbon atoms and accordingly is, for example, methyl, ethyl, propyl, isopropyl, n-butyl, isobutyl or tert.-butyl.

If $R^b$ or $R^{5a}$ is an alkyl group having from 1 to 24 carbon atoms, then these include the straight-chain or branched alkyl groups as indicated as examples of $R^1$, supplemented, for example, by eicosyl or docosyl. Alkyl groups having from 1 to 18 carbon atoms are preferred.

$R^{11}$, $R^{12}$ and $R^{13}$ are, for example, independently of one another, alkyl having from 1 to 12 carbon atoms, the alkyl groups being straight-chain or branched and there being mentioned by way of example: methyl, ethyl, propyl, isopropyl, n-butyl, isobutyl, tert.-butyl, pentyl, isopentyl, hexyl, heptyl, 3-heptyl, octyl, 2-ethylhexyl, nonyl, decyl, undecyl, dodecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl. The corresponding examples having from 1 to 8 carbon atoms are preferred.

$R^{6a}$, and $R^5$ and $R^6$, independently of one another, can advantageously be alkyl having from 1 to 12 carbon atoms. The alkyl group can be straight-chain or branched and examples can be taken from the corresponding list for $R^{11}$ and $R^{12}$ above.

Preferably, $R_A$ can be a $C_4$–$C_8$alkyl group and examples of such a group are n-butyl, isobutyl, tert.-butyl, pentyl, isopentyl, hexyl, heptyl, octyl, isooctyl, 2-ethylhexyl, 2-ethylbutyl, 1-methylpentyl, 1,3-dimethylbutyl, 1,1,3,3-tetramethylbutyl, 1-methylhexyl, isoheptyl or 1-methylheptyl.

Where isoC$_8$H$_{17}$ is mentioned, it may be understood as including also a mixture of isomers.

If $R^1$, $R^2$, $R^4$, $R^5$, $R^6$ or $R^{5a}$ is cycloalkyl having from 5 to 12 carbon atoms, then this includes, for example, cyclopentyl, cyclohexyl, cycloheptyl, cyclooctyl, cyclodecyl and cyclododecyl. Cyclohexyl is preferred.

$R^{6a}$ as cycloalkyl having from 5 to 8 carbon atoms can be cyclopentyl, cyclohexyl, cycloheptyl or cyclooctyl.

Furthermore, $R^5$ and $R^6$ are also $C_1$–$C_4$alkyl-substituted cycloalkyl having from 5 to 12 carbon atoms. Preferred are cycloalkyl having from 5 to 12 carbon atoms and are substituted by one, two or three $C_1$–$C_4$alkyl groups. Examples thereof are 2- or 4-methylcyclohexyl, dimethylcyclohexyl, trimethylcyclohexyl or tert.-butylcyclohexyl.

If $R^{6a}$ is phenyl substituted by one or more, preferably one, two or three, alkyl groups having a total of from 1 to 24 carbon atoms or $R_A$ is phenyl substituted by one or more, preferably one, two or three, alkyl groups having a total of from 1 to 20 carbon atoms, then examples of substituents $R^{6a}$ and $R_A$ may include methylphenyl, dimethylphenyl, trimethylphenyl, ethylphenyl, diethylphenyl, isopropylphenyl, tert.-butylphenyl, di-tert.-butylphenyl, methyl-di-tert.-butylphenyl, tert.-octylphenyl and di-tert.-octylphenyl.

Finally, $R^{12}$ and $R^{13}$ can form together with the carbon atom to which they are bonded a cycloalkyl ring having from 5 to 12 carbon atoms. Examples that may be mentioned are a cyclopentyl, cyclohexyl, cycloheptyl, cyclooctyl, cyclodecyl or cyclododecyl ring. A cyclohexyl ring is preferred.

If $R^1$, $R^2$, $R^5$ or $R^6$ is aralkyl having from 7 to 9 carbon atoms or from 7 to 10 carbon atoms, then examples thereof are benzyl, phenethyl, α-methylbenzyl or α,α-dimethylbenzyl. Benzyl is preferred.

If $R^4$ is an alkenyl group having from 2 to 18 carbon atoms, then examples thereof are vinyl, propenyl, allyl, butenyl, methallyl, hexenyl, decenyl or heptadecenyl.

The radical

can also be a hydrazine radical of formula —NH—NH$_2$, which may include the hydrazine hydrate radical.

For $R^5$ or $R^6$ as alkenyl having from 3 to 8 carbon atoms there come into consideration, for example, allyl, 2-methallyl, 2-butenyl or 2-hexenyl.

Compounds of formula I wherein n is 1 or 2 are preferred.

Advantageous compositions according to the invention contain at least one compound of formula I wherein $R^1$ is alkyl having from 1 to 18 carbon atoms, cycloalkyl having from 5 to 12 carbon atoms, phenyl or benzyl, $R^2$ is —H, alkyl having from 1 to 18 carbon atoms, cycloalkyl having from 5 to 12 carbon atoms, phenyl or benzyl, and $R^3$ is —H, and n is a number from 1 to 4 or 6, wherein, when n is 1, A is

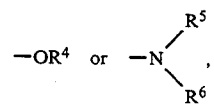

and $R^4$ is —H, alkyl having from 1 to 20 carbon atoms, cyclohexyl, alkenyl having from 2 to 18 carbon atoms or —CH₂CH₂—XR⁵ᵃ, and R⁵ is —H, alkyl having from 1 to 12 carbon atoms, phenyl, cyclohexyl, C₁–C₄alkyl-substituted cycloalkyl having from 5 to 12 carbon atoms, alkenyl having from 3 to 8 carbon atoms, benzyl or —NH₂, and R⁶ is —H or alkyl having from 1 to 12 carbon atoms, X is

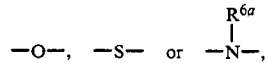

R⁵ᵃ is —H, alkyl having from 1 to 12 carbon atoms, phenyl, cyclohexyl or

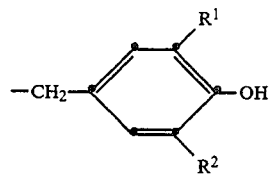

and R⁶ᵃ is alkyl having from 1 to 12 carbon atoms, phenyl, or phenyl substituted by one or more alkyl groups having a total of from 1 to 18 carbon atoms, or, when n is 2, A is —O—C$_x$H$_{2x}$—O—, —O—(CH₂CH₂O)$_a$CH₂CH₂O—, —O—CH₂—CH₂—B—CH₂—CH₂—O—,

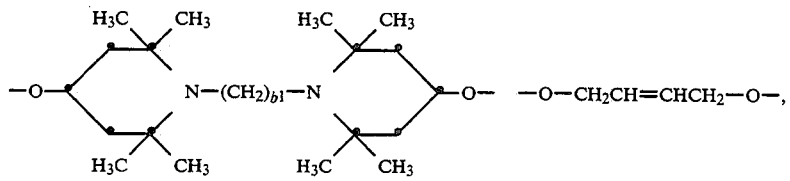

—O—CH₂CH₂NH—C—C—NH—CH₂CH₂—O—,
              ‖  ‖
              O  O

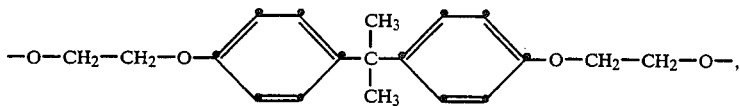

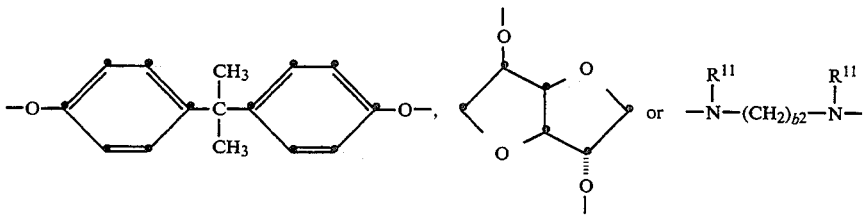

wherein a is a number from 1 to 12, x is a number from 2 to 12, B is

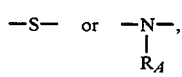

is alkyl having from 1 to 12 carbon atoms, phenyl, phenyl substituted by one or more alkyl groups having a total of from 1 to 18 carbon atoms or cyclohexyl, and R¹¹ is —H, alkyl having from 1 to 12 carbon atoms or phenyl, and b¹ is a number from 2 to 6 and b² is a number from 0 to 6, or, when n is 3, A is

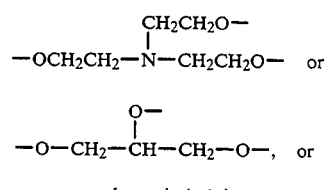

when n is 4, A is

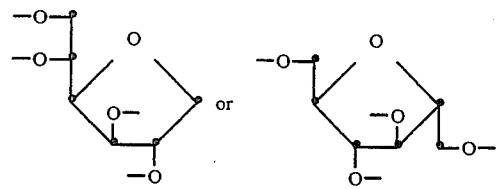

or, when n is 6, A is

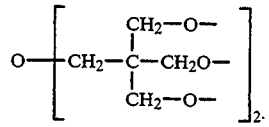

Especially advantageous compositions contain at least one compound of formula I wherein R¹ is alkyl having from 1 to 8 carbon atoms, cyclohexyl or phenyl, R² is —H, alkyl having from 1 to 8 carbon atoms, cyclohexyl or phenyl, and R³ is —H, and n is 1 and A is

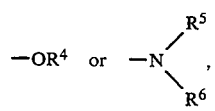

wherein $R^4$ is —H, alkyl having from 1 to 18 carbon atoms, cyclohexyl,

—CH$_2$CH=CH$_2$, —(CH$_2$)$_7$—CH=CH—(CH$_2$)$_7$CH$_3$,

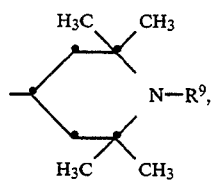

or —CH$_2$CH$_2$XR$^{5a}$, wherein $R^9$ is —H, alkyl having from 1 to 4 carbon atoms, —O., —O—alkyl having from 1 to 4 carbon atoms or cyclohexyl, X is

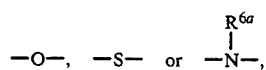

$R^{5a}$ is —H, alkyl having from 1 to 18 carbon atoms, phenyl,

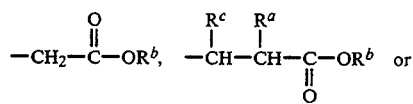

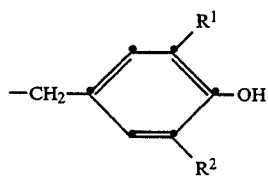

wherein $R^b$ is alkyl having from 1 to 24 carbon atoms, $R^a$ is —H or —CH$_3$, $R^c$ is —H and $R^{6a}$ is alkyl having from 1 to 12 carbon atoms or phenyl, and each of $R^5$ and $R^6$, independently of the other, is —H, alkyl having from 1 to 12 carbon atoms, phenyl or wherein $R^9$ is as defined above, or $R^5$ is —NH$_2$ and $R^6$ is —H, or n is 2, in which case A is —O—C$_x$H$_{2x}$—O— and x is 2 to 8.

Preferred compositions contain at least one compound of formula I wherein $R^1$ is tert.-butyl, $R^2$ is —H, methyl or tert.-butyl, and $R^3$ is —H, and n is 1, in which case A is

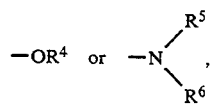

and $R^4$ is alkyl having from 1 to 18 carbon atoms,

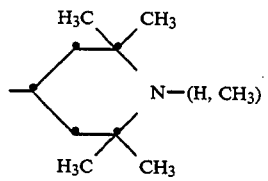

or —CH$_2$CH$_2$—SR$^{5a}$ wherein $R^{5a}$ is

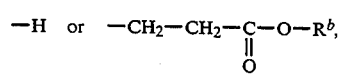

wherein $R^b$ is n-C$_4$H$_9$ to n-C$_8$H$_{17}$ or tert.-C$_4$H$_9$ to tert.-C$_8$H$_{17}$, or n is 2, in which case A is —O—C$_x$H$_{2x}$—O— and x is 2 to 8, or A is —O—(CH$_2$—CH$_2$—O—)$_a$—CH$_2$—CH$_2$—O— and a is 1 to 4, or A is —O—CH$_2$—CH$_2$—B—CH$_2$—CH$_2$—O— and B is

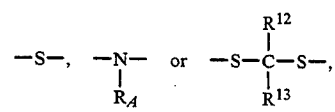

wherein $R_A$ is C$_4$–C$_8$alkyl or phenyl, $R^{12}$ is H or C$_1$–C$_8$alkyl and $R^{13}$ is H, C$_1$–C$_8$-alkyl or phenyl, or A is

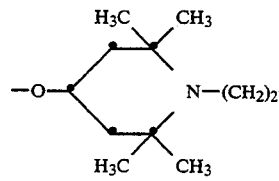 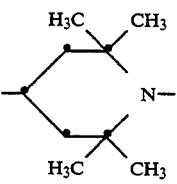 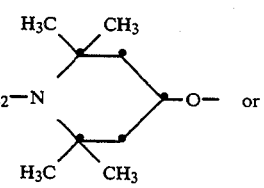

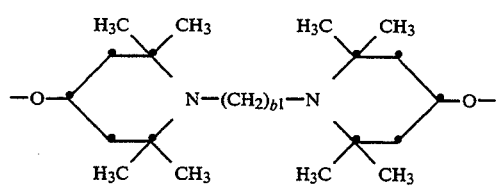

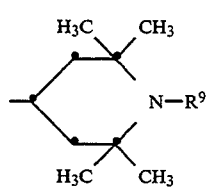

wherein b$^1$ is 2 to 6, or A is

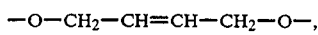

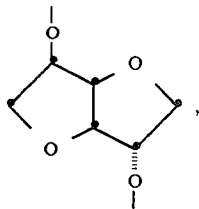

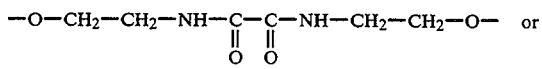

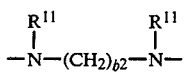

wherein $b^2$ is 0 to 6 and $R^{11}$ is —H or $C_1$-$C_8$alkyl.

Further preferred compositions contain at least one compound of formula I wherein $R^1$ is tert.-butyl, $R^2$ is —H, —$CH_3$ or tert.-butyl, and $R^3$ is —H and n is 1 and A is —$OR^4$ and $R^4$ is $C_1$-$C_{18}$alkyl.

Further preferred compositions include those containing at least one compound of formula I wherein $R^1$ is tert.-butyl, $R^2$ is —H, —$CH_3$ or tert.-butyl and $R^3$ is —H, and n is 2 and A is —O—$C_xH_{2x}$—O— and x is 2 to 6, or A is —O—($CH_2$—$CH_2$—O)$_a$—$CH_2$—$CH_2$—O— and a is 1, 2 or 3, or A is —O—$CH_2$—$CH_2$—B—$CH_2$—$CH_2$—O— and B is

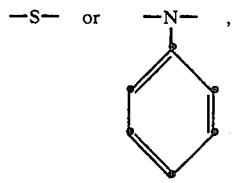

or A is

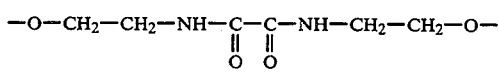

or A is —NH—NH—.

Also preferred is a composition containing at least one compound of formula I wherein $R^1$ is tert.-butyl, $R^2$ is —H, —$CH_3$ or tert.-butyl, $R^3$ is —H, n is 1 and A is —$OR^4$, wherein $R^4$ is $C_1$-$C_{18}$alkyl, or n is 2 and A is —O—$C_xH_{2x}$—O—, and x is 2 to 6 —O$CH_2$CH$_2$—S—$CH_2$CH$_2$O— or —O($CH_2$CH$_2$O)$_a$CH$_2$CH$_2$—O— and a is 1 to 4.

A composition of the above-mentioned type containing at least one compound of formula I wherein a is 1 or 2 is especially preferred.

Also preferred is a composition containing at least one compound of formula I wherein $R^1$ is tert.-butyl, $R^2$ is —H, —$CH_3$, tert.-butyl, and $R^3$ is —H and n is 3 and A is

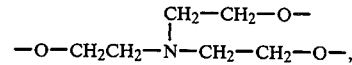

or n is 4 and A is

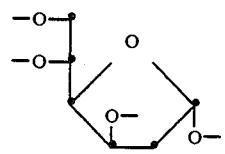

or n is 6 and A is

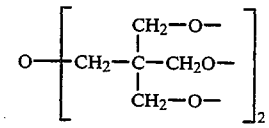

Particularly preferred are compositions containing at least one compound from the series of formulae

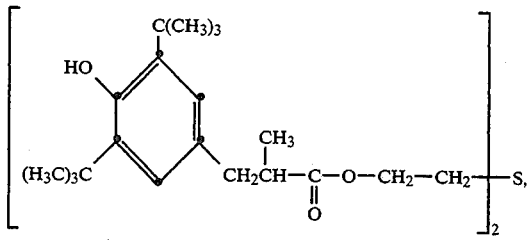

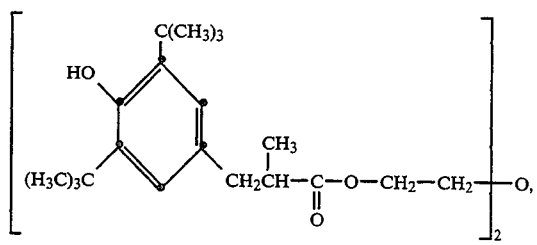

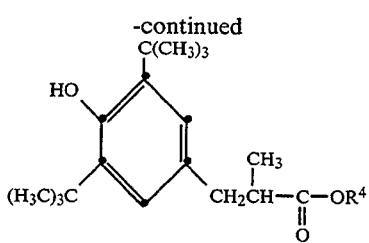

wherein $R^4$ is $C_1$-$C_{18}$alkyl and especially —$CH_3$, -n-$C_4H_9$, -iso$C_8H_{17}$, -n-$C_{12}H_{25}$ or -n-$C_{18}H_{37}$,

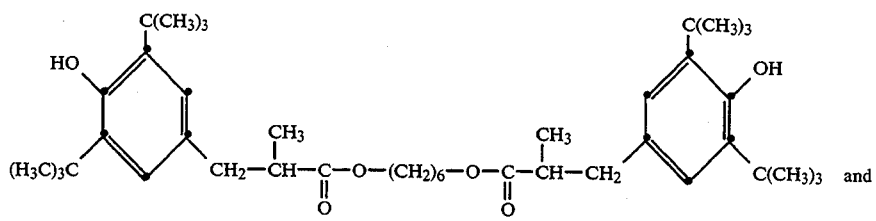 and

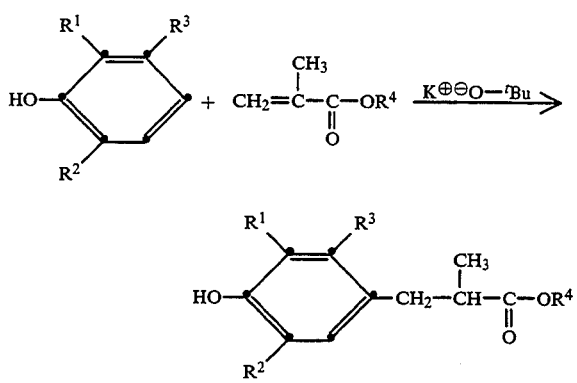

The above-mentioned individual compounds in lubricants of the group consisting of mineral oils, synthetic oils or mixtures thereof represent particularly valuable compositions.

The compounds of formula I can be prepared, for example, by a Michael addition, the reaction following the equation below:

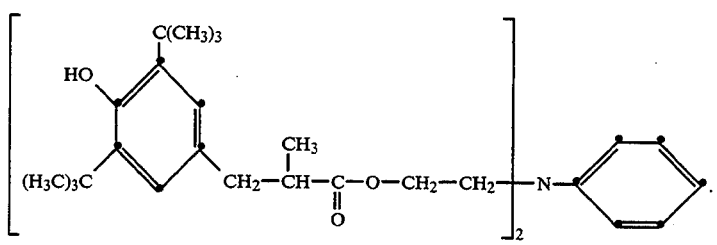

wherein $R^1$, $R^2$, $R^3$ and $R_4$ can be as defined above.

The process is carried out by reacting the alkyl-substituted phenol with the olefinic ester in stoichiometric excess in the presence of a catalytic amount of a base, for example a quaternary ammonium base, an alkali metal amide or an alkali metal alkanolate, at a temperature of from 150° to 220° C.

A detailed description of the process can be found, for example, in U.S. Pat. No. 4,529,809 which is mentioned at the beginning.

A further process for the preparation of compounds according to the invention is the transesterification that follows the general equation:

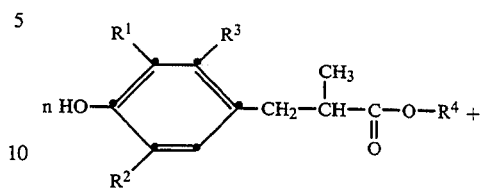

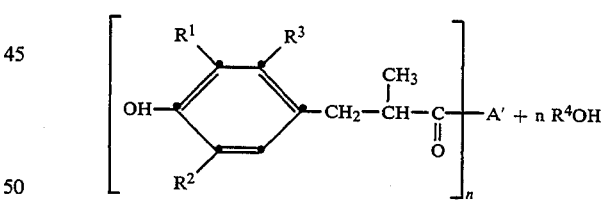

wherein $R^1$, $R^2$ and $R^3$ are as defined above, while A' has the same meaning as A with the exception of the radical —$NR^5R^6$. There are advantageously used starting esters in which $R^4$ is $C_1$-$C_4$alkyl, especially methyl, which, as described above, can likewise be prepared by reaction of a corresponding phenol with a methacrylate of formula

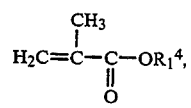

wherein $R_1^4$ is $C_1$-$C_4$alkyl.

Suitable catalysts are, for example, dibutyltin oxide Ti(—O-iso$C_3H_7$)$_4$, LiNH$_2$, LiH, LiOH, KOR, NaOR, LiOR wherein R is H or $C_1$-$C_{10}$alkyl, or

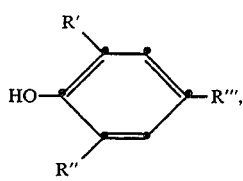

wherein each of R', R" and R''', independently of the others, is H or alkyl having from 1 to 10 carbon atoms.

The process is advantageously carried out in a solvent, such as benzene, toluene, xylene, dimethylformamide etc.

A further process for the preparation of compounds according to the invention follows the general equation for the esterification:

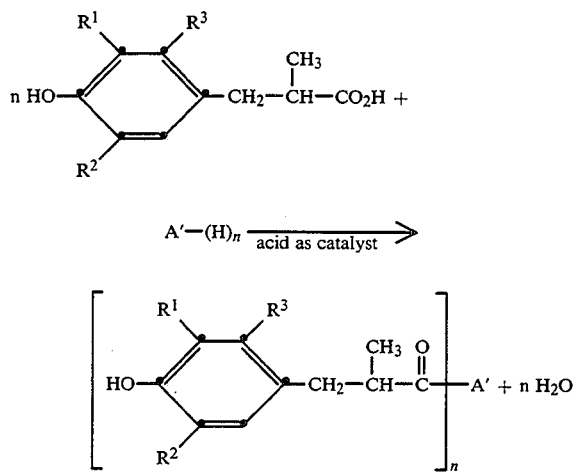

wherein $R^1$, $R^2$, $R^3$ and A' can be as defined above. The reaction is carried out in the presence of an acid as catalyst. Suitable catalysts are, for example, fuller's earth, such as Tosil L80S, or p-toluenesulfonic acid. The preparation of the carboxylic acid starting compounds can be effected by hydrolysis of compounds of formula

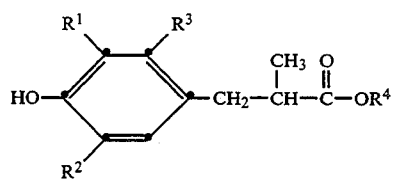

A process that is also suitable for the preparation of compounds in accordance with the present invention is also the reaction of a corresponding acid chloride with an alcohol or amine. The process can be described more accurately using the following reaction equation:

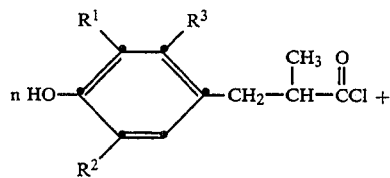

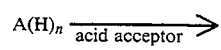

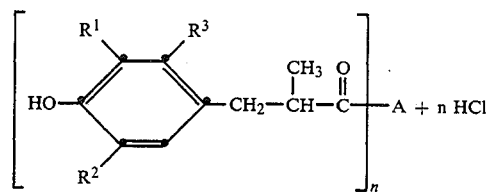

The meanings of $R^1$, $R^2$, $R^3$ and A are given above. As acid acceptor there may be used, for example, pyridine, triethylamine or an alkali metal hydroxide, such as NaOH or KOH.

Another process for the preparation of compounds in accordance with the present invention follows the equation:

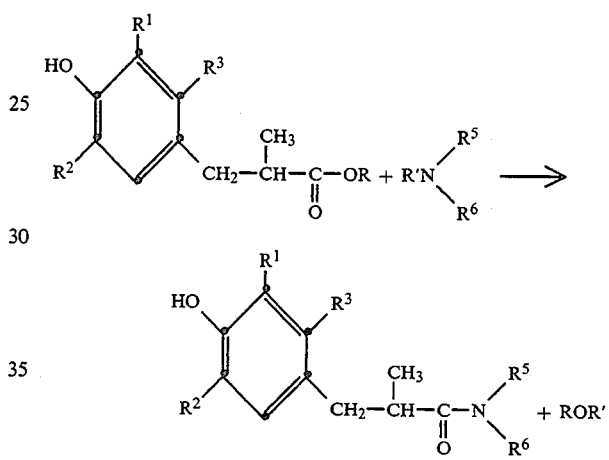

wherein R and R' have, for example, independently of one another, the same meaning as $R_1^4$ or are hydrogen. The reaction is effected by thermal reaction at, for example, 80°–190° C.

The compounds of formula I of the invention are excellently suitable for stabilising organic material, especially organic material that is sensitive to oxidative, thermal or actinic degradation.

The present invention therefore relates to compositions containing organic materials that are sensitive to oxidative, thermal or actinic degradation and at least one compound of formula I, and to the use of compounds of formula I for stabilising organic materials that are sensitive to oxidative, thermal or actinic degradation.

Advantageously the organic materials contain 0.01 to 10, for example, 0.05 to 5, preferably 0.05 to 3, especially 0.1 to 2% by weight, based on the organic material, of compounds of formula I.

The invention relates also to compositions that contain an organic material that is sensitive to oxidative, thermal or actinic degradation and especially a synthetic polymer or a functional fluid and at least one compound of formula I.

Further organic materials that can be stabilised according to the invention with the aid of the compound of formula I are, for example:

1. Polymers of mono- and di-olefins, for example polypropylene, polyisobutylene, polybutene-1, polymethylpentene-1, polyisoprene or polybutadiene, and polymers of cycloolefins, for example of cyclopentene or norbornene; also polyethylene (which can optionally be cross-linked), for example high density polyethylene (HDPE), low density polyethylene (LDPE), linear low density polyethylene (LLDPE).

2. Mixtures of the polymers mentioned under 1., for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and di-olefins with one another or with other vinyl monomers, for example ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene; also mixtures of such copolymers with one another and with polymers mentioned under 1., for example polypropylene-ethylene/propylene copolymers, LDPE-ethylene/vinyl acetate copolymers, LDPE-ethylene/acrylic acid copolymers, LLDPE-ethylene/vinyl acetate copolymers and LLDPE-ethylene/acrylic acid copolymers.

3a. Hydrocarbon resins (for example $C_5$–$C_9$) including hydrogenated modifications thereof (for example tackifier resins).

4. Polystyrene, poly-(p-methylstyrene), poly-(α-methylstyrene).

5. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic acid anhydride, styrene/acryonitrile/methacrylate; high-impact-strength mixtures consisting of styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/ethylenebutylene/styrene, or styrene/ethylene-propylene/styrene.

6. Graft copolymers of styrene or α-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic acid anhydride on polybutadiene; styrene, acrylonitrile and maleic acid anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 5., as known, for example, as so-called ABS, MBS, ASA or AES polymers.

7. Halogen-containing polymers, for example polychloroprene, chlorocaoutchouc, chlorinated or chlorosulfonated polyethylene, epichlorohydrin homopolymers and copolymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

8. Polymers derived from α,β-unsaturated acids and their derivatives, such as polyacrylates and polymethacrylates, polyacrylamides and polyacrylonitriles.

9. Copolymers of the monomers mentioned under 8. with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers derived from unsaturated alcohols and amines or their acyl derivatives or acetals, such as polyvinyl alcohol, polyvinyl acetate, stearate, benzoate, maleate, polyvinylbutyral, polyallyl phthalate, polyallylmelamine; and copolymers thereof with olefins mentioned under point 1.

11. Homo- and co-polymers of cyclic ethers, such as polyalkylene glycols, polyethylene oxide, polypropylene oxide or copolymers thereof with bis-glycidyl ethers.

12. Polyacetals, such as polyoxymethylene, and those polyoxymethylenes which contain comonomers, for example ethylene oxide; polyacetals modified with thermoplastic polyurethanes, acrylates or MBS.

13. Polyphenylene oxides and sulfides and mixtures thereof with styrene polymers or polyamides.

14. Polyurethanes derived from polyethers, polyesters and polybutadienes having terminal hydroxy groups on the one hand and aliphatic or aromatic polyisocyanates on the other hand, and their intermediates.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, polyamide 11, polyamide 12, aromatic polyamides derived from m-xylene, diamine and adipic acid; polyamides prepared from hexamethylenediamine and iso- and/or tere-phthalic acid and optionally an elastomer as modifier, for example poly-2,4,4-trimethylhexamethyleneterephthalamide, poly-m-phenylene-isophthalamide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified with EPDM or ABS and polyamides condensed during processing ("RIM polyamide systems").

16. Polyureas, polyimides, polyamide-imides and polybenzimidazoles.

17. Polyesters derived from dicarboxylic acids and di-alcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and block polyether esters derived from polyethers with terminal hydroxy groups; also polyesters modified with polycarbonates or MBS.

18. Polycarbonates and polyester carbonates.

19. Polysulfones, polyether sulfones and polyether ketones.

20. Cross-linked polymers derived from aldehydes on the one hand and phenols, urea or melamine on the other hand, such as phenol-formaldehyde, urea-formaldehyde and melamine-formaldehyde resins.

21. Drying and non-drying alkyd resins.

22. Unsaturated polyester resins derived from co-polyesters of saturated and unsaturated dicarboxylic acids with polyvalent alcohols, and vinyl compounds as cross-linking agents, and also their halogen-containing, difficultly combustible modifications.

23. Cross-linkable acrylic resins derived from substituted acrylic acid esters, for example from epoxy acrylates, urethane acrylates or polyester acrylates.

24. Alkyd resins, polyester resins and acrylate resins cross-linked with melamine resins, urea resins, polyisocyanates or epoxy resins.

25. Cross-linked epoxy resins derived from polyepoxides, for example from bis-glycidyl ethers or from cycloaliphatic diepoxides.

26. Natural polymers, such as cellulose, natural rubber, gelatine and the polymer-homologously chemically modified derivatives thereof, such as cellulose acetates, propionates and butyrates, and the cellulose ethers, such as methylcellulose; and also colophonium resins and derivatives.

27. Mixtures (polyblends) of the above-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

28. Natural and synthetic organic substances that are pure monomeric compounds or mixtures thereof, for example mineral oils, animal or vegetable fats, oils and waxes, or oils, waxes and fats based on synthetic esters (for example phthalates, adipates, phosphates or trimellitates), and also mixtures of synthetic esters with mineral oils in any desired weight ratios, for example as used as functional fluids or as spinning preparations, including the aqueous emulsions of spinning preparations.

29. Aqueous emulsions of natural or synthetic rubbers, for example natural latex rubber or latices of carboxylated styrene-butadiene copolymers.

Advantageous groups are the synthetic polymers, and preferred groups of plastics are those of the group consisting of the polyolefins, the elastomers, ABS, IPS, the polycarbonates, the polyimides, the polyesters, the polyacetals and the carboxylated SBR.

The incorporation of the stabiliser substances of the invention and, where applicable, of other additives into the organic material is effected according to known methods. For example, it can be effected by mixing in the products of the invention and, where applicable, other additives by the methods customary in the art before or during shaping, or alternatively by applying the dissolved or dispersed compounds to the polymer, where applicable with subsequent evaporation of the solvent. The products according to the invention can also be added to the materials to be stabilised in the form of a master batch which contains the products according to the invention, for example, in a concentration of from 2.5 to 25% by weight. The products according to the invention can also be added before or during polymerisation or before cross-linking.

Advantageously, the incorporation of the compounds of formula I can be effected by the following methods:
- as an emulsion or dispersion (for example to latices or emulsion polymers),
- as a dry mixture during the mixing of additional components or polymer mixtures,
- direct addition into the processing apparatus (for example extruder, kneader etc.),
- as a solution or melt.

The materials thus stabilised can be used in a great variety of forms, for example in the form of films, fibres, ribbons, moulding compositions, profiles or as binders for lacquers, adhesives or cements.

For example, in polyolefins the compounds of formula I exhibit extraordinarily good colour-enhancing properties.

In addition to the compounds of formula I, the above-mentioned organic materials and especially the synthetic polymers may also contain other additives. Examples of additional additives are:

1. Anti-oxidants 1.1. Alkylated monophenols, for example 2,6-di-tert.-butylphenol, 2,6-di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert.-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert.-butyl-4-methoxymethylphenol, 2,6-dinonyl-4-methylphenol.

1.2. Alkylated hydroquinones, for example 2,6-di-tert.-butyl-4-methoxyphenol, 2,5-di-tert.-butylhydroquinone, 2,5-di-tert.-amylhydroquinone, 2,6-diphenyl-4-octadecyloxyphenol.

1.3. Hydroxylated thiodiphenyl ethers, for example 2,2'-thio-bis-(6- tert.-butyl-4-methylphenol), 2,2'-thio-bis-(4-octylphenol), 4,4'-thio-bis-(6-tert.-butyl-3-methylphenol), 4,4'-thio-bis-(6-tert.-butyl-2methylphenol).

1.4. Alkylidene-bisphenols, for example 2,2'-methylene-bis-(6-tert.-butyl-4-methylphenol), 2,2'-methylene-bis-(6-tert.-butyl-4-ethylphenol), 2,2'-methylene-bis-[4-methyl-6-($\alpha$-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.-butylphenol), 2,2'- ethylidene-bis-(4,6-di-tert.-butylphenol), 2,2'-ethylidene-bis-(6-tert.-butyl-4-isobutylphenol), 2,2'-methylene-bis-[6-($\alpha$-methylbenzyl)-4-nonylphenol], 2,2'-methylene-bis-[6-($\alpha,\alpha$-dimethylbenzyl)-4-nonylphenol], 4,4'-methylene-bis-(2,6-di-tert.-butylphenol), 4,4'-methylene-bis-(6-tert-butyl-2-methylphenol), 1,1-bis-(5-tert.-butyl-4-hydroxy-2-methylphenyl)-butane, 2,6-bis-(3-tert.-butyl-5-methyl-2-hydroxybenzyl)-4-methylphenol, 1,1,3-tris-(5-tert.-butyl-4-hydroxy-2-methylphenyl)-butane, 1,1-bis-(5-tert.-butyl-4-hydroxy-2-methylphenyl)-3-n-dodecylmercaptobutane, ethylene glycol bis-[3,3-bis-(3'-tert.-butyl-4'-hydroxyphenyl)-butyrate], bis-(3-tert.-butyl-4-hydroxy-5-methylphenyl)-dicyclopentadiene, bis-[2-(3'-tert.-butyl-2'-hydroxy-5'-methylbenzyl)-6-tert.-butyl-4-methylphenyl]-terephthalate.

1.5. Benzyl compounds, for example 1,3,5-tris-(3,5-di-tert.-butyl-4-hydroxybenzyl)-2,4,6-trimethylbenzene, bis-(3,5-di-tert.-butyl-4-hydroxybenzyl)-sulfide, 3,5-di-tert.-butyl-4-hydroxybenzylmercaptoacetic acid isooctyl ester, bis-(4-tert.-butyl-3-hydroxy-2,6-dimethylbenzyl)-dithiol terephthalate, 1,3,5-tris-(3,5-di-tert.-butyl-4-hydroxybenzyl)-isocyanurate, 1,3,5-tris-(4-tert.-butyl-3-hydroxy-2,6-dimethylbenzyl)-isocyanurate, 3,5-di-tert.-butyl-4-hydroxybenzylphosphonic acid dioctadecyl ester, Ca salt of 3,5-di-tert.-butyl-4-hydroxybenzylphosphonic acid monoethyl ester, 1,3,5-tris-(3,5-dicyclohexyl-4-hydroxybenzyl)-isocyanurate.

1.6. Acylaminophenols, for example 4-hydroxylauric acid anilide, 4-hydroxystearic acid anilide, 2,4-bis-(octylmercapto)-6-(3,5-di-tert.-butyl-4-hydroxyanilino)-s-triazine, N-(3,5-di-tert.-butyl-4-hydroxyphenyl)-carbamic acid octyl ester.

1.7. Esters of β-(3,5-di-tert.-butyl-4-hydroxyphenyl)-propionic acid with mono- or poly-valent alcohols, for example with methanol, octadecanol, 1,6-hexanediol, neopentyl glycol, thiodiethylene glycol, diethylene glycol, triethylene glycol, pentaerythritol, tris-(hydroxyethyl)-isocyanurate, N,N'-bis-(hydroxyethyl)-oxalic acid diamide.

1.8. Esters of β-(5-tert.-butyl-4-hydroxy-3-methylphenyl)-propionic acid with mono- or poly-valent alcohols, for example with methanol, octadecanol, 1,6-hexanediol, neopentyl glycol, thiodiethylene glycol, diethylene glycol, triethylene glycol, pentaerythritol, tris-(hydroxyethyl)-isocyanurate, N,N'-bis-(hydroxyethyl)-oxalic acid diamide.

1.9. Esters of β-(3,5-dicyclohexyl-4-hydroxyphenyl)-propionic acid with mono- or poly-valent alcohols, for example with methanol, octadecanol, 1,6-hexanediol, neopentyl glycol, thiodiethylene glycol, diethylene glycol, triethylene glycol, pentaerythritol, tris-(hydroxyethyl)-isocyanurate, N,N'-bis-(hydroxyethyl)-oxalic acid diamide.

1.10. Amides of β-(3,5-di-tert.-butyl-4-hydroxyphenyl)-propionic acid, for example N,N'-bis-(3,5-di-tert.-butyl-4-hydroxyphenylpropionyl)-hexamethylenediamine, N,N'-bis-(3,5-di-tert.-butyl-4-hydroxyphenylpropionyl)-trimethylenediamine, N,N'-bis-(3,5-di-tert.-butyl-4-hydroxyphenylpropionyl)-hydrazine.

2. UV absorbers and light stabilising agents 2.1. 2-(2'-hydroxyphenyl)-benzotriazoles, for example the 5'-methyl, 3',5'-di-tert.-butyl, 5'-tert.-butyl, 5'-(1,1,3,3-tetramethylbutyl), 5-chloro-3',5'-di-tert.-butyl, 5-chloro-3'-tert.-butyl-5'-methyl, 3'-sec.-butyl-5'-tert.-butyl, 4'-octyloxy, 3',5'-di-tert.-amyl, 3',5'-bis-(α,α-dimethylbenzyl) derivative.

2.2. 2-hydroxybenzophenones, for example the 4-hydroxy, 4-methoxy, 4-octyloxy, 4-decyloxy, 4-dodecyloxy, 4-benzyloxy, 4,2', 4'-trihydroxy, 2'-hydroxy-4,4'-dimethoxy derivative.

2.3. Esters of unsubstituted or substituted benzoic acids, for example 4-tert.-butylphenylsalicylate, phenylsalicylate, octylphenylsalicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.-butyl-phenyl ester, 3,5-di-tert.-butyl-4-hydroxybenzoic acid hexadecyl ester.

2.4. Acrylates, for example α-cyano-β,β-diphenylacrylic acid ethyl ester or isooctyl ester, α-methoxycarbonylcinnamic acid methyl ester, α-cyano-β-methyl-p-methoxycinnamic acid methyl ester or butyl ester, α-methoxycarbonyl-p-methoxycinnamic acid methyl ester, N-(β-methoxycarbonyl-β-cyanovinyl)-2-methylindoline.

2.5. Nickel compounds, for example nickel complexes of 2,2'-thio-bis-[4-(1,1,3,3-tetramethylbutyl)-phenol], such as the 1:1 or 1:2 complex, optionally with additional ligands, such as n-butylamine, triethanolamine or N-cyclohexyl diethanolamine, nickel dibutyl dithiocarbamate, nickel salts of 4-hydroxy-3,5-di-tert.-butylbenzylphosphonic acid monoalkyl esters, such as of the methyl or ethyl ester, nickel complexes of ketoximes, such as of 2-hydroxy-4-methylphenylundecyl ketoxime, nickel complexes of 1-phenyl-4-lauroyl-5-hydroxypyrazole, optionally with additional ligands.

2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.-butyl-4-hydroxybenzylmalonic acid bis-(1,2,2,6,6-pentamethylpiperidyl)-ester, condensation product of 1-hydroxyethyl-2,2,6,6-tetramethyl-4-hydroxypiperidine and succinic acid, condensation product of N,N'-bis-(2,2,6,6-tetramethyl-4-piperidyl)-hexamethylenediamine and 4-tert.-octylamino-2,6-dichloro-1,3,5-s-triazine, tris-(2,2,6,6-tetramethyl-4-piperidyl)-nitrolotriacetate, tetrakis-(2,2,6,6-tetramethyl-4-piperidyl)-1,2,3,4-butanetetraoate, 1,1'-(1,2-ethanediyl)-bis-(3,3,5,5-tetramethylpiperazinone).

2.7. Oxalic acid diamides, for example 4,4'-dioctyloxy-oxanilide, 2,2'-dioctyloxy-5,5'-di-tert.-butyloxanilide, 2,2'-didodecyloxy-5,5'-di-tert.-butyloxanilide, 2-ethoxy-2'-ethyloxanilide, N,N'-bis-(3-dimethylaminopropyl)-oxalamide, 2-ethoxy-5-tert.-butyl-2'-ethyloxanilide and a mixture thereof with 2-ethoxy-2'-ethyl-5,4'-di-tert.-butyloxanilide, mixtures of o- and p-methoxy- and of o- and p-ethoxy-disubstituted oxanilides.

3. Metal deactivators, for example N,N'-diphenyloxalic acid diamide, N-salicylal-N'-salicyloylhydrazine, N,N'-bis-(salicyloyl)-hydrazine, N,N'-bis-(3,5-di-tert.-butyl-4-hydroxyphenylpropionyl)-hydrazine, 3-salicyloylamino-1,2,4-triazole, bis-(benzylidene)-oxalic acid dihydrazide.

4. Phosphites and phosphonites, for example triphenylphosphite, diphenylalkylphosphites, phenyldialkylphosphites, tris-(nonylphenyl)-phosphite, trilaurylphosphite, trioctadecylphosphite, distearyl-pentaerythritol diphosphite, tris-(2,4-di-tert.-butylphenyl)-phosphite, diisodecylpentaerythritol diphosphite, bis-(2,4-di-tert.-butylphenyl)-pentaerythritol diphosphite, tristearyl sorbitol triphosphite, tetrakis-(2,4-di-tert.-butylphenyl-4,4'-biphenylene diphosphonite, 3,9-bis-(2,4-di-tert.-butylphenoxy)-2,4,8,10-tetraoxa-3,9-diphosphaspiro[5.5]undecane.

5. Peroxide-decomposing compounds, for example esters of β-thio-dipropionic acid, for example of lauryl, stearyl, myristyl or tridecyl esters, mercaptobenzimidazole, the zinc salt of 2-mercaptobenzimidazole, zinc dibutyl dithiocarbamate, dioctadecyl disulfide, pentaerythritol tetrakis-(β-dodecylmercapto)-propionate.

6. Polyamide stabilisers, for example copper salts in combination with iodides and/or phosphorus compounds and salts of divalent manganese.

7. Basic costabilisers, for example melamine, polyvinylpyrrolidone, dicyanodiamide, triallyl cyanurate, urea derivatives, hydrazine derivatives, amines, polyamides, polyurethanes, alkali metal and alkaline earth metal salts of higher fatty acids, for example Ca stearate, Zn stearate, Mg stearate, Na ricinoleate, K palmitate, antimony pyrocatecholate or tin pyrocatecholate.

8. Nucleation agents, for example 4-tert.-butylbenzoic acid, adipic acid, diphenylacetic acid.

9. Fillers and reinforcers, for example calcium carbonate, silicates, glass fibres, asbestos, talcum, kaolin, mica, barium sulfate, metal oxides and hydroxides, soot, graphite.

10. Other additives, for example plasticisers, glidants, emulsifiers, pigments, optical brighteners, flameproofing agents, antistatic agents, propellants.

Advantageous compositions according to the present invention are accordingly, for example, those which contain a) synthetic polymers and b) at least one compound of formula I, as described above. The synthetic polymer in the said composition is preferably a polyolefin.

Other advantageous compositions contain a) a functional fluid preferably from the group consisting of lubricants, hydraulic fluids and metal working fluids and b) at least one compound of formula I, as described above.

Lubricants are especially preferred and, of those, the mineral oils, the synthetic oils or mixtures thereof are of particular interest.

As functional fluids from the group consisting of lubricants, hydraulic fluids and metal working fluids there are used the products known per se.

The lubricants and hydraulic fluids that come into consideration are known to the person skilled in the art and are described, for example, in Dieter Klamann "Schmierstoffe und verwandte Produkte", Verlag Chemie, Weinheim, 1982, in Schewe-Kobek, "Das Schmiermittel-Taschenbuch", Dr. Alfred Hüthig-Verlag, Heidelberg, 1974, or in "Ullmanns Encyclopädie der technischen Chemie", Vol. 13, pages 85–94 (Verlag Chemie, Weinheim, 1977).

Examples thereof are lubricants and hydraulic fluids based on mineral oils, or synthetic lubricants or hydraulic fluids, especially those which are carboxylic acid ester derivatives and are used at temperatures of 200° C. and above.

Examples of synthetic lubricants include lubricants based on a diester of a divalent acid with a monovalent alcohol, for example dioctyl sebacate or dinonyl adipate, a triester of trimethylol propane with a monovalent acid or with a mixture of such acids, for example trimethylolpropane tripelargonate, trimethylolpropane tricaprylate or mixtures thereof, a tetraester of pentaerythritol with a monovalent acid or with a mixture of such acids, for example pentaerythritol tetracaprylate, or a complex ester of monovalent and divalent acids with polyvalent alcohols, for example a complex ester of trimethylolpropane with caprylic or sebacic acid or of a mixture thereof.

Especially suitable, in addition to mineral oils, are, for example, poly-α-olefins, lubricants based on esters, phosphates, glycols, polyglycols and polyalkylene glycols, and mixtures thereof with water.

The compounds of formula I are readily soluble in lubricants and are therefore especially suitable as additives to lubricants and attention is drawn to their surprisingly good anti-oxidative and anti-corrosive action.

The compounds of formula I are able to display their superior properties, for example, in lubricants for internal combustion engines, for example internal combustion engines according to the Otto principle. For example, in lubricating oils the compounds of formula I prevent the formation of sludge or reduce sludge formation to a surprising extent.

It is also possible to prepare so-called master batches.

The compounds of formula I are effective even in very small amounts as additives in lubricants. They are advantageously mixed with the lubricants in an amount of from 0.01 to 5% by weight, preferably in an amount of from 0.05 to 3% by weight, and especially preferably in an amount of from 0.1 to 2% by weight, in each case based on the lubricant.

The lubricants may, in addition, contain other additives which are added in order further to improve the basic properties of lubricants; these include: anti-oxidants, metal passivators, rust inhibitors, viscosity index enhancers, pour-point depressors, dispersants, detergents, high pressure additives and anti-wear additives.

For example, a number of such compounds can be found in the above list "1. Anti-oxidants", especially under points 1.1 to 1.10. Furthermore, other additives may be mentioned by way of example:

Examples of aminic anti-oxidants: N,N'-diisopropyl-p-phenylenediamine, N,N'-di-sec.-butyl-p-phenylenediamine, N,N'-bis-(1,4-dimethylpentyl)-p-phenylenediamine, N,N'-bis-(1-ethyl-3-methylpentyl)-p-phenylenediamine, N,N'-bis-(1-methylheptyl)-p-phenylenediamine, N,N'-dicyclohexyl-p-phenylenediamine, N,N'-diphenyl-p-phenylenediamine, N,N'-di-(naphth-2-yl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec.-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert.-octyldiphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)-amine, 2,6-di-tert.-butyl-4-dimethylaminomethyl-phenol, 2,4'-diaminodiphenylmethane, 4,4'-diaminodiphenylmethane, N,N,N',N'-tetramethyl-4,4'-diaminodiphenylmethane, 1,2-di-[(2-methylphenyl)-amino]-ethane, 1,2-di-(phenylamino)-propane, (o-tolyl)-biguanide, di-[4-(1',3'-dimethylbutyl)-phenyl]-amine, tert.-octylated N-phenyl-1-naphthylamine, a mixture of mono- and di-alkylated tert.-butyl-/tert.-octyl-diphenylamines, 2,3-dihydro-3,3-dimethyl-4H-1,4-benzothiazine, phenothiazine, N-allylphenothiazine.

Examples of further anti-oxidants: aliphatic or aromatic phosphites, esters of thiodipropionic acid or thiodiacetic acid, or salts of dithiocarbamic or dithiophosphoric acid.

Examples of metal passivators, for example for copper, are: triazoles, benzotriazoles and derivatives thereof, tolutriazoles and derivatives thereof, 2-mercaptobenzothiazole, 2-mercaptobenzotriazole, 2,5-dimercaptobenzotriazole, 2,5-dimercaptobenzothiadiazole, 5,5'-methylene-bis-benzotriazole, 4,5,6,7-tetrahydrobenzotriazole, salicylidene-propylenediamine, salicylaminoguanidine and salts thereof.

Examples of rust inhibitors are: a) Organic acids, their esters, metal salts and anhydrides, for example: N-oleoylsarcosine, sorbitan monooleate, lead naphthenate, alkenylsuccinic acid anhydride, for example dodecenylsuccinic acid anhydride, alkenylsuccinic acid partial esters and partial amides, 4-nonylphenoxyacetic acid. b) Nitrogen-containing compounds, for example: I. Primary, secondary or tertiary aliphatic or cycloaliphatic amines and amine salts of organic and inorganic acids, for example oil-soluble alkylammonium carboxylates. II. Heterocyclic compounds, for example: substituted imidazolines and oxazolines. c) Phosphorous-containing compounds, for example: amine salts of phosphoric acid partial esters or phosphonic acid partial esters, zinc dialkyl dithiophosphates. d) Sulfur-containing compounds, for example: barium dinonylnaphthalenesulfonates, calcium petroleum sulfonates.

Examples of viscosity index enhancers are: polyacrylates, polymethacrylates, vinylpyrrolidone/methacrylate copolymers, polyvinylpyrrolidones, polybutenes, olefin copolymers, styrene/acrylate copolymers, polyethers.

Examples of pour-point depressors are: polymethacrylate, alkylated naphthalene derivatives.

Examples of dispersants/surfactants/detergents are: polybutenylsuccinic acid amides or imides, polybutenylphosphonic acid derivatives, basic magnesium, calcium and barium sulfonates and phenolates.

Examples of high pressure additives/anti-wear additives are: sulfur- and/or phosphorus- and/or halogen-containing compounds, such as sulfated vegetable oils, zinc dialkyl dithiophosphates, tritolyl phosphate, chlorinated paraffins, alkyl- and aryl-di- and tri-sulfides, triphenyl phosphorothionates, diethanolaminomethyltolyltriazole, di-(2-ethylhexyl)-aminomethyltolyltriazole.

The present invention also includes novel compounds of general formula Ia

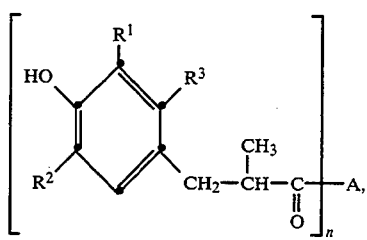

wherein $R^1$ is alkyl having from 1 to 18 carbon atoms, cycloalkyl having from 5 to 12 carbon atoms, phenyl or aralkyl having from 7 to 9 carbon atoms, $R^2$ is —H, alkyl having from 1 to 18 carbon atoms, cycloalkyl having from 5 to 12 carbon atoms, phenyl or aralkyl having from 7 to 9 carbon atoms, and $R^3$ is —H or $CH_3$, and n is a number from 1 to 4 or 6, and, when n is 1, A is

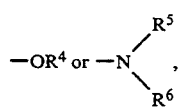

and $R^4$ is —H, alkyl having from 5 to 45 carbon atoms, cycloalkyl having from 5 to 12 carbon atoms, alkenyl having from 2 to 18 carbon atoms,

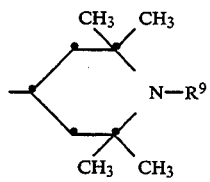

or —$CH_2CH_2$—$XR^{5a}$ and each of $R^5$ and $R^6$, independently of the other, is —H, alkyl having from 1 to 20 carbon atoms, phenyl, cycloalkyl having from 5 to 12 carbon atoms, $C_1$-$C_4$alkyl-substituted cycloalkyl having from 5 to 12 carbon atoms, alkenyl having from 3 to 8 carbon atoms, aralkyl having from 7 to 10 carbon atoms or

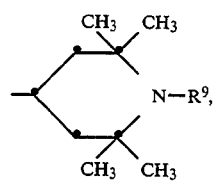

and, in addition, $R^5$ may be —$NH_2$, $R^9$ is —H, alkyl having from 1 to 8 carbon atoms,

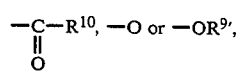

wherein $R^{9'}$ is —H, alkyl having from 1 to 25 carbon atoms or

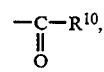

X is

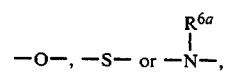

$R^{5a}$ is

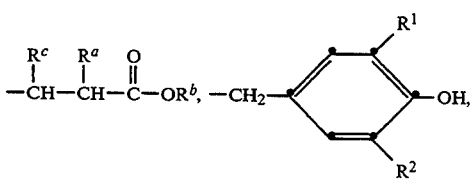

—H, alkyl having from 1 to 24 carbon atoms, phenyl, cycloalkyl having from 5 to 12 carbon atoms or

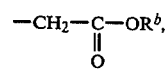

and $R^{10}$ is alkyl having from 1 to 20 carbon atoms, $R^a$ is —H or —$CH_3$, $R^b$ is —H or alkyl having from 1 to 24 carbon atoms and $R^c$ is —H or —$CH_3$, with the proviso that $R^a$ and $R^c$ are not —$CH_3$ at the same time, and $R^{6a}$ is alkyl having from 1 to 18 carbon atoms, phenyl, phenyl substituted by one or more alkyl groups having a total of from 1 to 24 carbon atoms, or $C_5$-$C_8$cycloalkyl, or, when n is 2, A is —O—$C_xH_{2x}$—O—, —O—$(CH_2CH_2O)_aCH_2CH_2O$—, —O—$CH_2$—$CH_2$—B—$CH_2$—$CH_2$—O—,

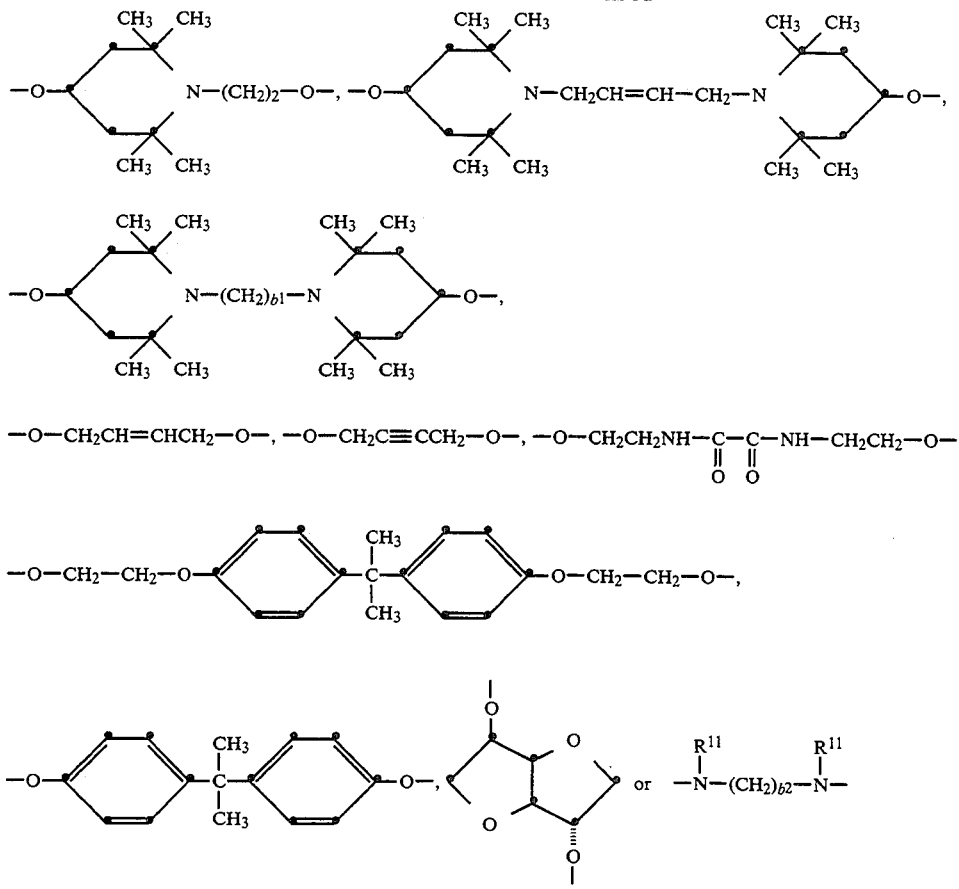

wherein a is a number from 1 to 30, x is a number from 2 to 20, B is

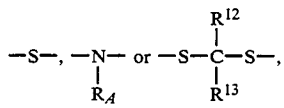

$R_A$ is alkyl having from 1 to 20 carbon atoms, phenyl, phenyl substituted by one or more alkyl groups having a total of from 1 to 20 carbon atoms, cyclohexyl or

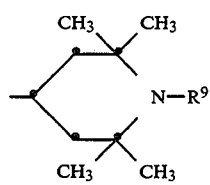

and each of $R^{11}$, $R^{12}$ and $R^{13}$, independently of the others, is —H, alkyl having from 1 to 12 carbon atoms or phenyl, or $R^{12}$ and $R^{13}$ together with the carbon atom to which they are bonded form a cycloalkyl ring having from 5 to 12 carbon atoms, $b^1$ is a number from 2 to 10 and $b^2$ is a number from 0 to 6, or, when n is 3, A is

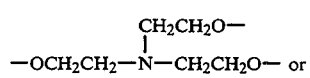

-continued

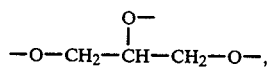

or, when n is 4, A is

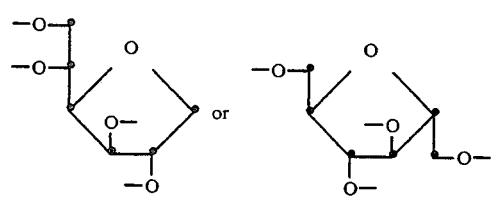

or, when n is 6, A is

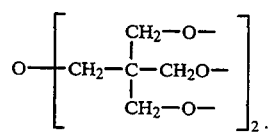

Advantageous compounds of formula Ia are those wherein $R^1$ is alkyl having from 1 to 18 carbon atoms, cycloalkyl having from 5 to 12 carbon atoms, phenyl or benzyl, $R^2$ is —H, alkyl having from 1 to 18 carbon atoms, cycloalkyl having from 5 to 12 carbon atoms, phenyl or benzyl, and $R^3$ is —H, and n is a number from 1 to 4 or 6, wherein, when n is 1, A is

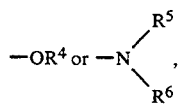

and $R^4$ is —H, alkyl having from 5 to 20 carbon atoms, cyclohexyl, alkenyl having from 2 to 18 carbon atoms or —CH$_2$CH$_2$—XR$^{5a}$, and $R^5$ is —H, alkyl having from 1 to 12 carbon atoms, phenyl, cyclohexyl, C$_1$-C$_4$alkyl-substituted cycloalkyl having from 5 to 12 carbon atoms, alkenyl having from 3 to 8 carbon atoms, benzyl or —NH$_2$, and $R^6$ is —H or alkyl having from 1 to 12 carbon atoms, X is

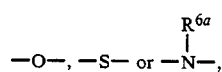

$R^{5a}$ is —H, alkyl having from 1 to 12 carbon atoms, phenyl, cyclohexyl or

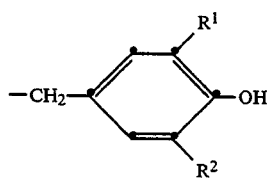

and $R^{6a}$ is alkyl having from 1 to 12 carbon atoms, phenyl, or phenyl substituted by one or more alkyl groups having a total of from 1 to 18 carbon atoms, or, when n is 2, A is

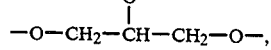

is alkyl having from 1 to 12 carbon atoms, phenyl, phenyl substituted by one or more alkyl groups having a total of from 1 to 18 carbon atoms or cyclohexyl, and $R^{11}$ is —H, alkyl having from 1 to 12 carbon atoms or phenyl, and $b^1$ is a number from 2 to 6 and $b^2$ is a number from 0 to 6, or, when n is 3, A is

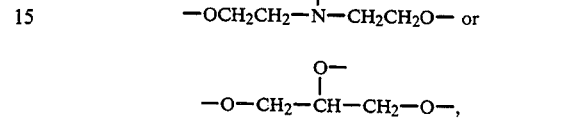

or, when n is 4, A is

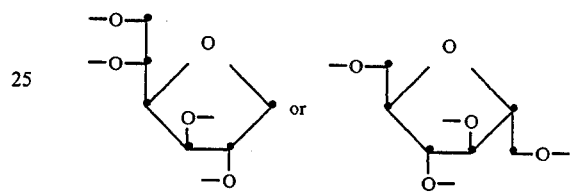

or, when n is 6, A is

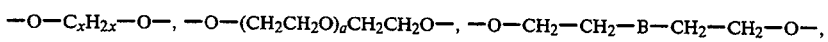

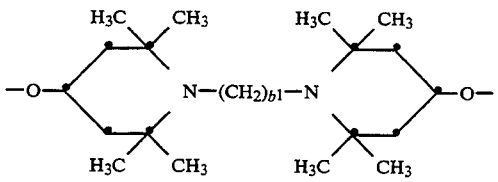

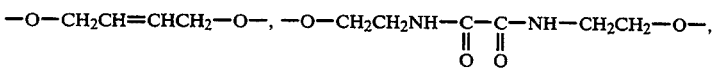

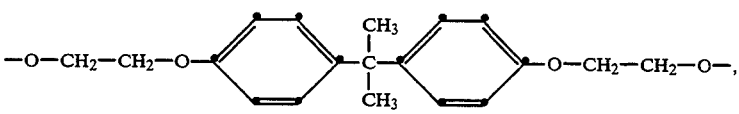

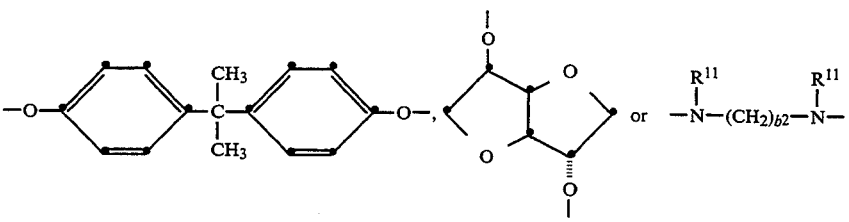

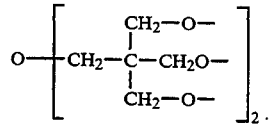

wherein a is a number from 1 to 12, x is a number from 2 to 12, B is

Especially advantageous compounds of formula Ia are those wherein $R^1$ is alkyl having from 1 to 8 carbon atoms, cyclohexyl or phenyl, $R^2$ is —H, alkyl having from 1 to 8 carbon atoms, cyclohexyl or phenyl, and $R^3$ is —H, and n is 1 and A is

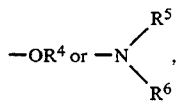

wherein $R^4$ is —H alkyl having from 5 to 18 carbon atoms, cyclohexyl,

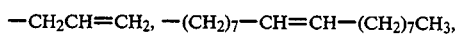

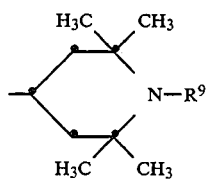

or —CH$_2$CH$_2$XR$^{5a}$, wherein $R^9$ is —H, alkyl having from 1 to 4 carbon atoms, —O., —O—alkyl having from 1 to 4 carbon atoms or cyclohexyl, X is

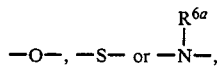

$R^{6a}$ is —H, alkyl having from 1 to 18 carbon atoms, phenyl,

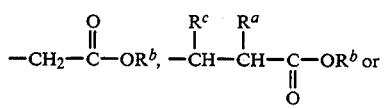

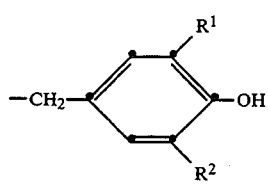

wherein $R^b$ is alkyl having from 1 to 24 carbon atoms, $R^a$ is —H or —CH$_3$, $R^c$ is —H and $R^{6a}$ is alkyl having from 1 to 12 carbon atoms or phenyl, and each of $R^5$ and $R^6$, independently of the other, is —H, alkyl having from 1 to 12 carbon atoms, phenyl, or

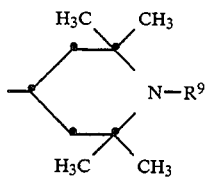

wherein $R^9$ is as defined above, or $R^5$ is —NH$_2$ and $R^6$ is —H, or n is 2, in which case A is —O—C$_x$H$_{2x}$—O— and x is 2 to 8.

Preferred are compounds of formula Ia wherein $R^1$ is tert.-butyl, $R^2$ is —H, methyl or tert.-butyl, and $R^3$ is —H, and n is 1, in which case A is

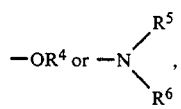

and $R^4$ is alkyl having from 6 to 18 carbon atoms,

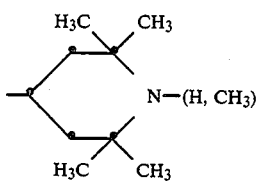

or —CH$_2$CH$_2$—SR$^{5a}$ wherein $R^{5a}$ is

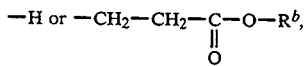

wherein $R^b$ is n-C$_4$H$_9$ to n-C$_8$H$_{17}$ or tert.-C$_4$H$_9$ to tert.-C$_8$H$_{17}$, or n is 2, in which case A is —O—C$_x$H$_{2x}$—O— and x is 2 to 8 or A is —O—(CH$_2$—CH$_2$—O—)$_a$—CH$_2$—CH$_2$—O— and a is 1 to 4, or A is —O—CH$_2$—CH$_2$—B—CH$_2$—CH$_2$—O— and B is

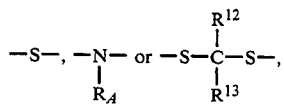

wherein $R_A$ is C$_4$-C$_8$alkyl or phenyl, $R^{12}$ is H or C$_1$-C$_8$alkyl and $R^{13}$ is H, C$_1$-C$_8$alkyl or phenyl, or A is

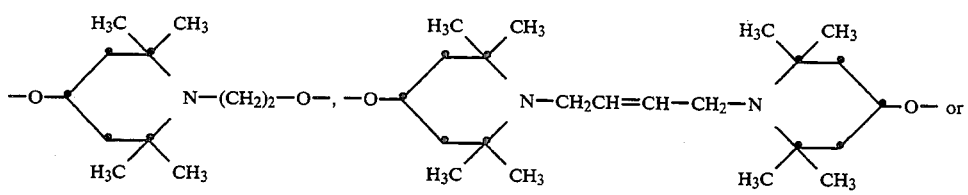

[Structure: piperidine-N-(CH₂)_{b1}-N-piperidine bridge with tetramethyl groups and -O- substituents]

wherein $b^1$ is 2 to 6, or A is $$-O-CH_2-CH=CH-CH_2-O-,$$

$$-O-CH_2-C\equiv C-CH_2-O-,$$

[bicyclic sugar-like structure with O substituents], $$-O-CH_2-CH_2-NH-\underset{\underset{O}{\|}}{C}-\underset{\underset{O}{\|}}{C}-NH-CH_2-CH_2-O- \text{ or}$$

$$-\underset{\underset{R^{11}}{|}}{N}-(CH_2)_{b2}-\underset{\underset{R^{11}}{|}}{N}-$$

wherein $b^2$ is 0 to 6 and $R^{11}$ is —H or $C_1$-$C_8$alkyl.

Further preferred compounds of formula Ia are those wherein $R^1$ is tert.-butyl, $R^2$ is —H, —CH₃ or tert.-butyl and $R^3$ is —H and n is 1 and A is —OR⁴ and R⁴ is $C_6$-$C_{18}$ alkyl.

Other compounds of formula Ia include those wherein $R^1$ is tert.-butyl, $R^2$ is —H, —CH₃ or tert.-butyl and $R^3$ is —H, and n is 2 and A is —O—$C_xH_{2x}$—O— and and x is 2 to 6, or A is —O—(CH₂—CH₂—O)_a—CH₂—CH₂—O— and a is 1, 2 or 3, or A is —O—CH₂—CH₂—B—CH₂—CH₂—O— and B $$-S- \text{ or } -\underset{\text{phenyl}}{N}-,$$

or A is $$-O-CH_2-CH_2-NH-\underset{\underset{O}{\|}}{C}-\underset{\underset{O}{\|}}{C}-NH-CH_2-CH_2-O-$$

or A is —NH—NH—.

Also preferred are compounds of formula Ia wherein $R^1$ is tert.-butyl, $R^2$ is —H, —CH₃ or tert.-butyl, $R^3$ is —H, n is 1 and A is —OR⁴, wherein R⁴ is $C_6$-$C_{18}$alkyl, or n is 2 and A is —O—$C_xH_{2x}$—O— and x is 2 to 6, —OCH₂CH₂—S—CH₂CH₂O— or —O(CH₂CH₂O)_aCH₂CH₂—O— and a is 1 to 4.

Compounds of formula Ia of the above-mentioned type wherein a is 1 or 2 are especially preferred.

Also preferred are compounds of formula Ia of the above-mentioned type wherein R⁴ is alkyl having from 9 to 18 carbon atoms.

Also preferred are compounds of formula Ia wherein $R^1$ is tert.-butyl, $R^2$ is —H, —CH₃, tert.-butyl and $R^3$ is —H and n is 3 and A is $$-O-CH_2CH_2-\underset{\underset{CH_2CH_2-O-}{|}}{N}-CH_2CH_2-O-,$$

or n is 4 and A is

[sugar-like ring with four —O— substituents]

or n is 6 and A is $$O-\left[-CH_2-\underset{\underset{CH_2-O-}{|}}{\overset{\overset{CH_2-O-}{|}}{C}}-CH_2O-\right]_2.$$

Particularly preferred are compounds from the series having the formulae $$\left[HO-\text{Ar}(C(CH_3)_3)((H_3C)_3C)-CH_2CH(CH_3)-C(=O)-O-CH_2-CH_2-\right]_2 S,$$

$$\left[HO-\text{Ar}(C(CH_3)_3)((H_3C)_3C)-CH_2CH(CH_3)-C(=O)-O-CH_2-CH_2-\right]_2 O,$$

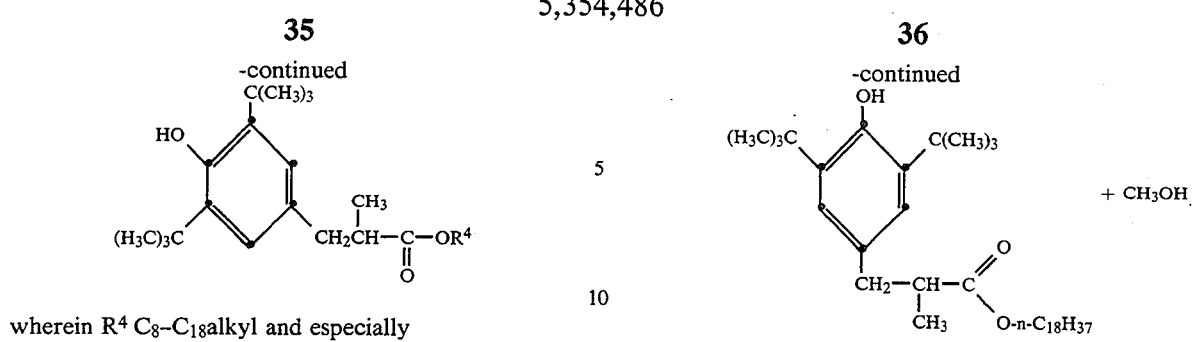

wherein $R^4$ $C_8$–$C_{18}$alkyl and especially

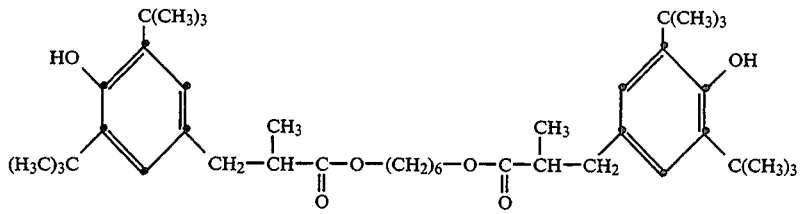

and

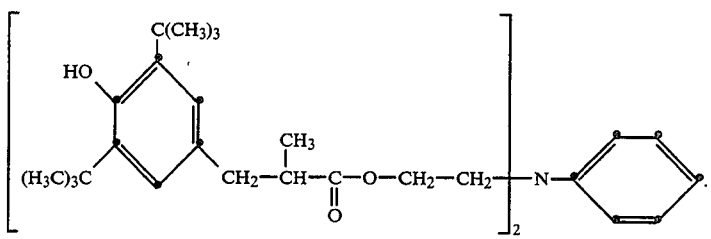

The scope of the present invention also includes the use of compounds of formula I in accordance with the above description as anti-oxidants in organic materials that are sensitive to oxidative, thermal or actinic degradation. The materials per se and also their preferred groups and compounds are defined above.

The use of the compounds of formulae I and Ia in lubricants is especially preferred.

The following Examples further illustrate the present invention but do not limit the scope thereof. Unless indicated to the contrary, parts and percentages always relate to weight.

EXAMPLE 1

Octadecyl-2-methyl-3-(3',5'-di-tert.-butyl-4'-hydroxyphenyl)-propionate

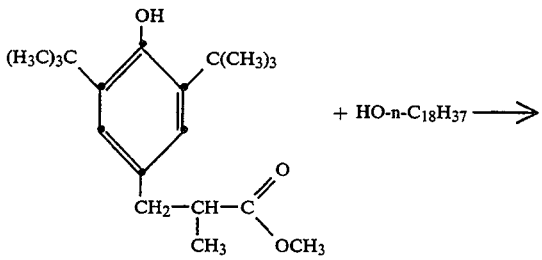

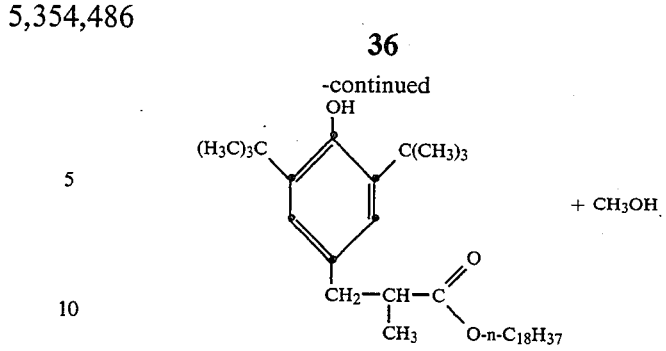

30.6 g (0.1 mol) of methyl-2-methyl-3-(3',5'-di-tert.-butyl-4'-hydroxyphenyl)-propionate and 27 g (0.1 mol) of 1-n-octadecanol are placed in a 4-necked glass flask and heated to 100° C. Then 0.25 g (1 mol %) of dibutyltin oxide is added and the mixture is heated to 180° C., with methanol being split off. The temperature is maintained at 180° C. for 6 hours.

The reaction mixture is neutralised with HCl (20%) and dried under a high vacuum.

52.4 g=96.2% of the theoretical yield of a slightly yellowish oil are obtained, the oil crystallising slowly. The melting point is then above 40° C.

Analysis: calculated 79.35% C 11.84% H found 79.57% C 11.68% H

EXAMPLE 2 n-Nonyl-2-methyl-3-(3',5'-di-tert.-butyl-4'-hydroxyphenyl)-propionate

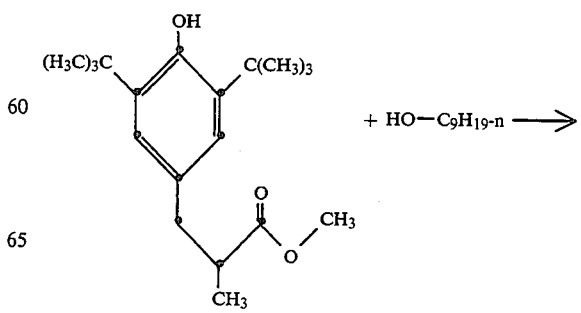

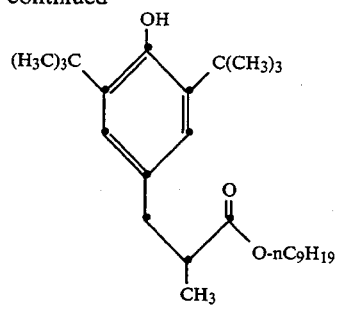

EXAMPLE 3

By reaction of isononyl alcohol, after a reaction period of 7 hours at 140° C., a yellowish oil containing 96.8% isononyl-2-methyl-3-(3',5'-di-tert.-butyl-4'-hydroxyphenyl)-propionate is obtained.

Analysis: calculated 77.46% C 11.08% H found 77.33% C 11% H

EXAMPLE 4

Diethylene glycol bis-[2-methyl-3-(3',5'-di-tert.-butyl-4'-hydroxyphenyl)-propionate]

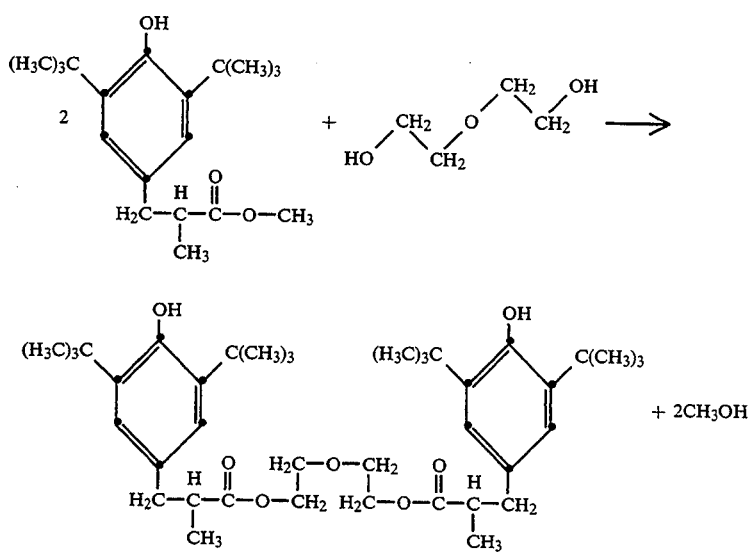

30.6 g of methyl-2-methyl-3-(3',5'-di-tert.-butyl-4'-hydroxyphenyl)-propionate and 14.4 g of n-nonyl alcohol are placed in a 100 ml sulfonating flask and heated to 100° C. 0.2 g of dibutyltin oxide is added and the temperature is increased to 150° C. Methyl alcohol is split off from a temperature of 125° C. The reaction is maintained at 150° C. for 6 hours.

The batch is dissolved in 60 ml of toluene, concentrated in a rotary evaporator and dried for 2 hours at 80° C. under a high vacuum.

39.4 g=94% of the theoretical yield of a slightly yellowish viscous oil are obtained.

Analysis: calculated 77.46% C 11.08% H found 77.35% C 10.93% H

The reaction is repeated analogously to Example 2; according to:

61.2 g (0.2 mol) of methyl-2-methyl-3-(3',5'-di-tert.-butyl-4'-hydroxyphenyl)-propionate and 10.6 g (0.1 mol) of diethylene glycol are placed in a 4-necked glass flask and heated to 100° C. Then 0.5 g=1 mol % of dibutyltin oxide is added and the reaction mixture is heated to 180° C., with methanol being split off. The temperature is maintained for 5 hours. Working up is effected by drying under a high vacuum.

64.2 g=98% of the theoretical yield of a brown viscous oil are obtained. This oil is then purified by column chromatography, a slightly yellowish viscous oil being obtained in a yield of 79.4% of the amount used.

Analysis: calculated 73.26% C 9.54% H found 73.51% C 9.38% H

EXAMPLE 5

Thiodiethylene glycol bis-[2-methyl-3-(3',5'-di-tert.-butyl-4'-hydroxyphenyl)-propionate]

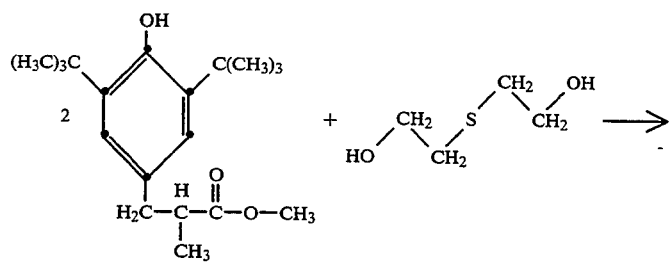

-continued

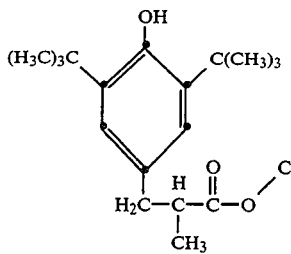
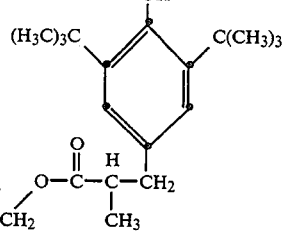

+ 2CH₃OH 91.9 g (0.3 mol) of methyl-2-methyl-3-(3',5'-di-tert.-butyl-4'-hydroxyphenyl)-propionate and 18.3 g (0.15 mol) of thiodiethylene glycol are placed in a 4-necked glass flask and heated to 100° C. 0.4 g of dibutyltin oxide=0.5 mol % is added and the mixture is heated to 180° C., with methanol being split off. The temperature is maintained at 180° C. for 6 hours.

After washing with water and drying under a high vacuum, 96.3 g=95.7% of the theoretical yield of a brown oil are obtained.

The brown oil is then purified by column chromatography, a yield of 72.4% of the amount used being obtained in the form of a light-brown viscous oil.

Analysis: calculated 71.60% C 9.31% H 4.78% S found 71.66% C 9.08% H 4.90% S

EXAMPLE 6

Dodecyl-2-methyl-3-(3',5'-di-tert.-butyl-4'-hydroxyphenyl)-propionate

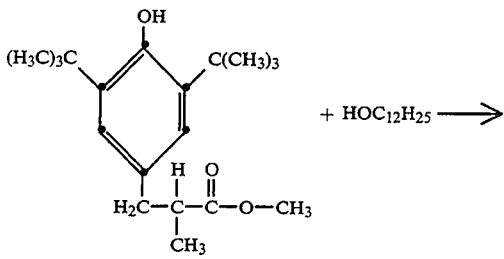

30.6 g (0.1 mol) of methyl-2-methyl-3-(3',5'-di-tert.-butyl-4'-hydroxyphenyl)-propionate and 18.6 g (0.1 mol) of 1-dodecanol are placed in a 4-necked glass flask and heated to 100° C., then 0.25 g=1 mol % of dibutyltin oxide is added and the mixture is heated further to 180° C., with methanol being split off. The reaction mixture is maintained at 180° C. for 6 hours.

The mixture is then dried under a high vacuum. 45.8 g=99.3% of the theoretical yield of a slightly yellowish oil are obtained.

Analysis: calculated 78.20% C 11.38% H found 78.32% C 11.27% H

EXAMPLE 7

2-Ethylhexyl-[2-methyl-3-(3',5'-di-tert.-butyl-4'-hydroxyphenyl)-propionate]

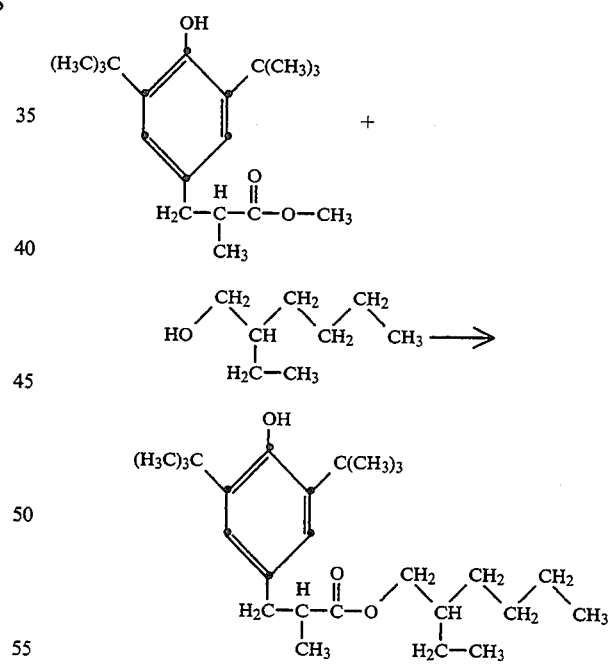

61.3 g (0.2 mol) of methyl-2-methyl-3-(3',5'-di-tert.-butyl-4'-hydroxyphenyl)-propionate and 26 g (0.2 mol) of 2-ethyl-1-hexanol are placed in a 4-necked glass flask and heated to 100° C. Then 1 g (2 mol %) of dibutyltin oxide is added and the temperature is increased to 180° C., with methanol being split off. The reaction mixture is maintained at 180° C. for 9 hours. The end product is obtained in pure form, without working up, as a slightly yellowish resin in a yield of 79.4 g=98.2% of the theoretical yield.

Analysis: calculated 77.18% C 10.96% H found 77.05% C 11.03% H

EXAMPLE 8

1,6-Hexanediol bis-[2-methyl-3-(3',5'-di-tert.-butyl-4'-hydroxyphenyl)-propionate]

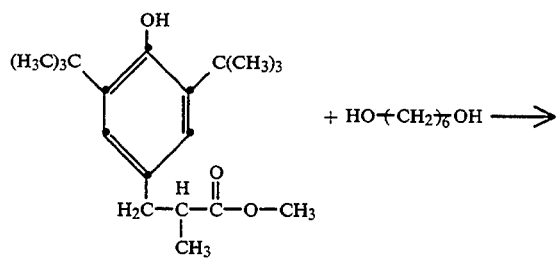
+ HO—(CH₂)₆—OH ⟶

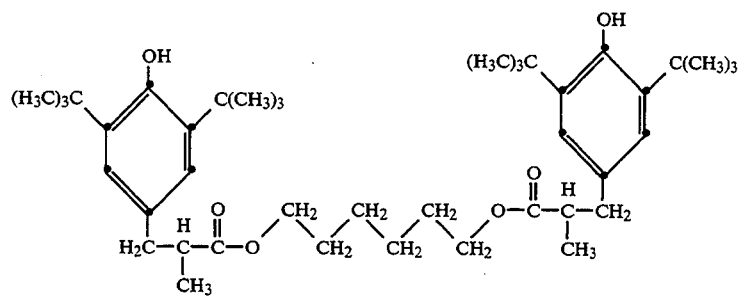

46 g (0.15 mol) of methyl-2-methyl-3-(3',5'-di-tert.-butyl-4'-hydroxyphenyl)-propionate and 8.9 g (0.075 mol) of 1,6-hexanediol are placed in a 200 ml 4-necked glass flask and heated to 100° C. Then 0.38 g=2 mol % of dibutyltin oxide is added and the reaction mixture is then heated to 180° C., with methanol being split off. The reaction is maintained at 180° C. for 6 hours. The subsequent working up is effected by crystallisation of the batch from 100 ml of a mixture of isopropanol and water (7:3), filtration with suction and washing with 2 ×30 ml of a cold isopropanol/water mixture (7:3) and drying in an oven at 50° C.

The yield is 24.7 g=49.4% of the theoretical yield of a light-beige pulverulent product.

Analysis: calculated 75.63% C 9.97% H found 75.85% C 9.97% H

EXAMPLE 9

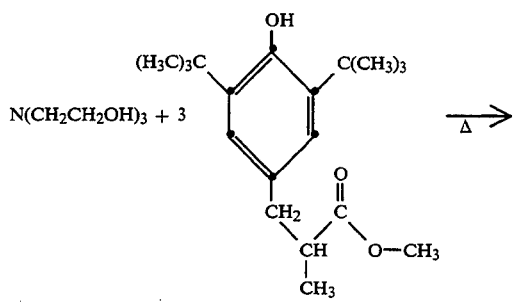

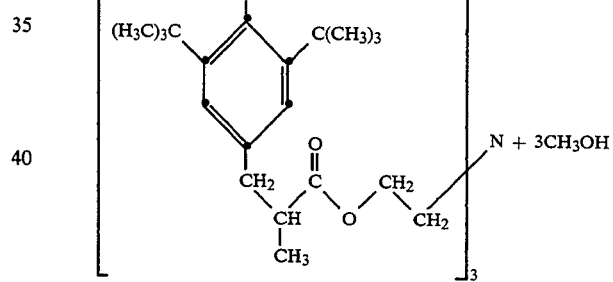

4.5 g of N-triethanolamine and 30.6 g of methyl-2-methyl-3-(3',5'-di-tert.-butyl-4'-hydroxyphenyl)-propionate are placed in a 100 ml sulfonating flask having a descending "Liebig" condenser under a gentle current of nitrogen. The mixture is heated to 120° C. and 0.25 g of dibutyltin oxide is added, and then the temperature is increased to 160° C., with MeOH being split off. The reaction temperature is maintained at 160° C. for 6 hours.

The batch is cooled to 80° C., then taken up in 60 ml of toluene and concentrated in a rotary evaporator. 26.8 g of a light-brown oil are obtained.

After purification by "flash" chromatography using toluene:ethyl acetate=9:1 as solvent, 23.6 g=81.1% of the theoretical yield of a light-brown oil are obtained.

| | Analysis: | |
|---|---|---|
| found | calculated | |
| 74.32 | 74.11 | % C |
| 9.65 | 9.64 | % H |
| 1.52 | 1.44 | % N |

EXAMPLE 10

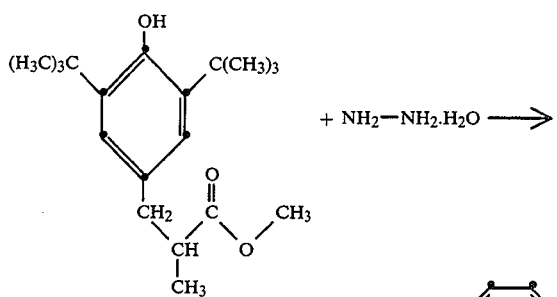

+ NH₂—NH₂.H₂O ⟶

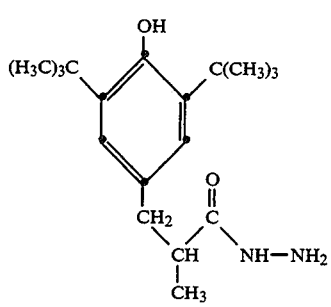

46 g of methyl-2-methyl-3-(3',5'-di-tert.-butyl-4'-hydroxyphenyl)-propionate are placed in 100 ml of ethanol and, at room temperature, added dropwise within a period of 30 minutes to a clear slightly yellowish solution of 7.5 g of hydrazine hydrate. The temperature is increased, the ethanol is distilled off and then the reaction temperature is increased to 100° C., a thick unstirrable paste being obtained. After cooling to room temperature and mixing with hexane, the mixture is filtered with suction and dried in an oven at 60°.

39.8 g=86.5% of the theoretical yield of a white powder having a melting point of 128° C. are obtained.

| | Analysis: | |
|---|---|---|
| found | calculated | |
| 70.72 | 70.55 | % C |
| 10.03 | 9.87 | % H |
| 9.03 | 9.14 | % N |

EXAMPLE 11

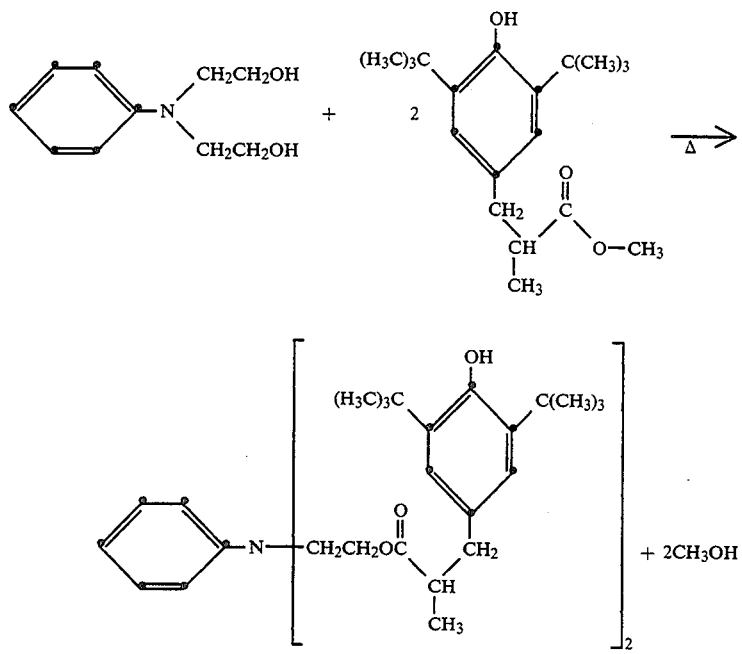

18.1 g of N-phenyldiethanolamine and 61.3 g of methyl-2-methyl-3-(3',5'-di-tert.-butyl-4'-hydroxyphenyl)-propionate are placed in a 350 ml sulfonating flask having a descending "Liebig" condenser under a gentle current of nitrogen. The reaction mixture is heated to 120° C., 0.5 g of dibutyltin oxide is added and the temperature is increased to 160° C., with MeOH being split off. The mixture is left for 8 hours at 150° C. to complete the reaction. The batch is cooled to 80° C. and taken up in 100 ml of toluene, then concentrated in a rotary evaporator, yielding 74 g of a brown oil.

Purification is effected by means of "flash" chromatography using toluene:ethyl acetate 9:1 as solvent.

59.5 g=81.5% of the theoretical yield of an orange oil are obtained.

| | Analysis: | |
|---|---|---|
| found | calculated | |
| 75.68 | 75.83 | % C |
| 9.25 | 9.26 | % H |
| 1.92 | 1.87 | % N |

EXAMPLE 12

Some of the compounds according to Examples 1 to 11 are tested for their suitability as stabilisers against the oxidative degradation of a lubricating oil.

A commercially available mineral lubricating oil (Mobil 15 SS 4) is mixed with 0.05% by weight of a commercially available corrosion inhibitor of the alkenylsuccinic acid semiester type.

The individual stabilisers, corresponding to the preceding Examples, are then added to the prepared oil in an amount of 0.25% by weight, based on the oil, and the resulting stabilised oils are subjected to an oxidation test.

The test method is known as the TOST test (oxidation characteristics of mineral oil Mobil 15 SS 4, ASTM D 934/DIN 51587/IP 157).

The oil to be tested is heated at 95° C. in the presence of water, oxygen, an iron/copper catalyst and the stabiliser for 500 hours. Then the acid value TAN (in mg of KOH consumption per g of test oil) and the sludge (in mg of residue per batch) are determined. The results are given in Table 1.

| Stabiliser according to | 500 hours TOST | |
|---|---|---|
| | TAN (mg KOH/g oil) | SLUDGE (mg) |
| Example 1 | 0.11 | 22 |
| Example 2 | 0.20 | 103 |
| Example 3 | 0.30 | 76 |
| Example 4 | 0.06 | 30 |
| Example 7 | 0.09 | 72 |
| Example 8 | 0.07 | 33 |
| without | >2.0 | >1000 |

What is claimed is:

1. A composition comprising (a) at least one functional fluid subject to oxidative, thermal or actinic degradation, and (b) at least one compound of formula I

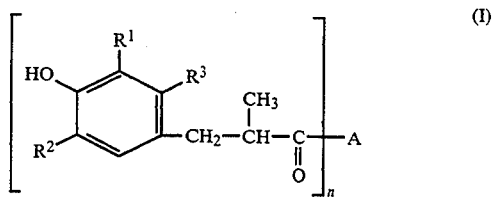

wherein $R^1$ is alkyl having 1 to 8 carbon atoms, cyclohexyl or phenyl, $R^2$ is hydrogen, alkyl having 1 to 8 carbon atoms, cyclohexyl or phenyl, $R^3$ is hydrogen, n is 1, and A is $-OR^4$ where $R^4$ is hydrogen or alkyl having 9 to 18 carbon atoms.

2. A composition according to claim 1, containing at least one compound of formula I wherein $R^1$ is tert.-butyl, $R^2$ is $-H$, $-CH_3$ or tert.-butyl, and $R^3$ is $-H$ and n is 1 and A is $-OR^4$ and $R^4$ is $C_9$-$C_{18}$ alkyl.

3. A composition according to claim 1 containing a) a lubricant selected from the group consisting of mineral oils, synthetic oils or a mixture thereof and b) at least one compound of formula I according to claim 1.

4. Process of improving the anti-oxidant properties of lubricants by incorporation of at least one compound of formula I according to claim 1 into said lubricant.

5. A composition according to claim 1 wherein said compound of formula I is octadecyl 2-methyl-3-(3,5-di-tert-butyl-4-hydroxyphenyl)-propionate.

6. A composition according to claim 1, containing at least one compound of the formula

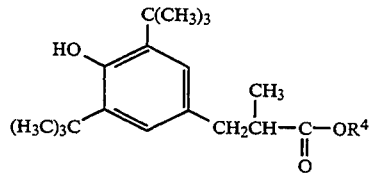

wherein $R^4$ is $C_1$-$C_{18}$ alkyl.

* * * * *